United States Patent
Bade et al.

(10) Patent No.: US 12,376,777 B1
(45) Date of Patent: Aug. 5, 2025

(54) SYSTEMS AND METHODS FOR TRANSFORMING ELECTROCARDIOGRAM IMAGES FOR USE IN ONE OR MORE MACHINE LEARNING MODELS

(71) Applicant: Anumana, Inc., Cambridge, MA (US)

(72) Inventors: Sairam Bade, Suryapet (IN); Yash Mishra, Bangalore (IN); Shiva Verma, Bangalore (IN); Uddeshya Upadhyay, Bengaluru (IN); Ashim Prasad, Bangalore (IN); Rakesh Barve, Bengaluru (IN); Samir Awasthi, Boston, MA (US); Shashi Kant, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/641,217

(22) Filed: Apr. 19, 2024

(51) Int. Cl.
| | |
|---|---|
| *A61B 5/389* | (2021.01) |
| *A61B 5/257* | (2021.01) |
| *A61B 5/308* | (2021.01) |
| *G06N 20/00* | (2019.01) |

(52) U.S. Cl.
CPC ............. *A61B 5/308* (2021.01); *G06N 20/00* (2019.01)

(58) Field of Classification Search
CPC ................................ G06N 20/00; A61B 5/308
See application file for complete search history.

(56) References Cited

U.S. PATENT DOCUMENTS

| | | | |
|---|---|---|---|
| 10,346,721 | B2 | 7/2019 | Albright et al. |
| 2020/0342968 | A1* | 10/2020 | Avinash ................. G06N 3/045 |
| 2021/0169417 | A1* | 6/2021 | Burton ................. A61B 5/4857 |
| 2021/0209757 | A1* | 7/2021 | Min ..................... G06V 10/764 |
| 2021/0304891 | A1* | 9/2021 | Kozloski ................ G16H 50/20 |
| 2023/0165505 | A1 | 6/2023 | Babaeizadeh |

FOREIGN PATENT DOCUMENTS

| | | |
|---|---|---|
| CN | 115919325 A | 4/2023 |
| CN | 116172514 A | 5/2023 |

* cited by examiner

*Primary Examiner* — Brandon S Cole
(74) *Attorney, Agent, or Firm* — Caldwell Intellectual Property Law

(57) ABSTRACT

A system for transforming electrocardiogram images for use in one or more machine learning models, the system including at least a processor configured to receive paired data including a plurality of ECG images correlated to a plurality of standardized images, wherein each ECG image of the plurality of ECG images is correlated with each standardized image of the plurality of standardized images, train an ECG transformation model as a function of the paired data, wherein training the transformation model includes adjusting one or more parameter values of the ECG transformation model as a function of a comparison between at least one predicted standardized image and at least one standardized image of the plurality of standardized images, receive non-conforming data, generate standardized data as a function of the ECG transformation model and the non-conforming data and train an ECG machine learning model as a function of the standardized data.

20 Claims, 8 Drawing Sheets

SYSTEMS AND METHODS FOR TRANSFORMING ELECTROCARDIOGRAM IMAGES FOR USE IN ONE OR MORE MACHINE LEARNING MODELS

FIELD OF THE INVENTION

The present invention generally relates to the field of machine learning. In particular, the present invention is directed to transforming electrocardiogram images for use in one or more machine learning models.

BACKGROUND

Building machine learning models can be challenging due to the varying quality of inputs received. In addition to predicting outputs, low quality inputs may skew results or cause inputs to be misinterpreted by the machine learning model. Current systems trained with training data of varying quality may generate inaccurate results due to variations in the inputs.

SUMMARY OF THE DISCLOSURE

In an aspect a system for transforming electrocardiogram images for use in one or more machine learning models is described. The system includes at least a processor and a memory communicatively connected to the at least a processor. The memory contains instructions configuring the at least a processor to receive paired data including a plurality of ECG images correlated to a plurality of standardized images, wherein each ECG image of the plurality of ECG images is correlated with each standardized image of the plurality of standardized images, train an ECG transformation model as a function of the paired data, wherein training the transformation model includes adjusting one or more parameter values of the ECG transformation model as a function of a comparison between at least one predicted standardized image and at least one standardized image of the plurality of standardized images, receive non-conforming data, generate standardized data as a function of the ECG transformation model and the non-conforming data and train an ECG machine learning model as a function of the standardized data.

In another aspect, a method for transforming electrocardiogram images for use in one or more machine learning models is described. The method includes receiving, by at least a processor, paired data including a plurality of ECG images correlated to a plurality of standardized images, wherein each ECG image of the plurality of ECG images is correlated with each standardized image of the plurality of standardized images, training, by the at least a processor, an ECG transformation model as a function of the paired data, wherein training the transformation model includes adjusting one or more parameter values of the ECG transformation model as a function of a comparison between at least one predicted standardized image and at least one standardized image of the plurality of standardized images, receiving, by the at least a processor, non-conforming data;

generating, by the at least a processor, standardized data as a function of the ECG transformation model and the non-conforming data and training, by the at least a processor, an ECG machine learning model as a function of the standardized data.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Electrocardiogram (ECG) Paper prints can come from different printed sources like Thermal printer, laser printer, dot-matrix printer, ink-jet printer, ink-tank printer etc. These printed papers can then be converted to digital images. The conversion to digital image itself can be done by using a scanner of different quality at different DPIs. The printed paper can also be converted to digital images by taking a photo of it using a camera (standalone camera or mobile phone camera) or scanner. Again, the photo can be taken using a camera/scanner of different qualities. Another way to get digital images can be by taking a screenshot or clicking a photo from a computer screen. Various prediction/generation models may be built on digital images of ECGs. Some examples of these models are disease prediction, parameter prediction, raw signal extraction, report generation etc. Building any prediction/generation models based on these ECG images can be challenging due to the varied quality of input ECG images. Especially in many cases the image quality would be poor (due to poor camera quality, poor lighting, non-uniform lighting, skewness, angle, focus, motion artifacts, folds/creases in the paper etc.). To overcome this problem, one or more approaches are described in this disclosure. Embodiments of this disclosure discuss transforming input ECG images to high quality ECG images and building all downstream tasks using this high quality ECG image One or more than one transformation models can be built to transform an input ECG image into a good quality image (e.g., an in-silicon image as described in further detail below). With the help of an ECG transformation model as described below, one can build all downstream models (disease, report generation, parameter prediction, signal extraction etc.) using computer generated images. At deployment setup one can use ECG transformation model to convert ECG coming from different sources and of different quality into computer generated quality image and then feed it to the downstream model.

Figure 1:
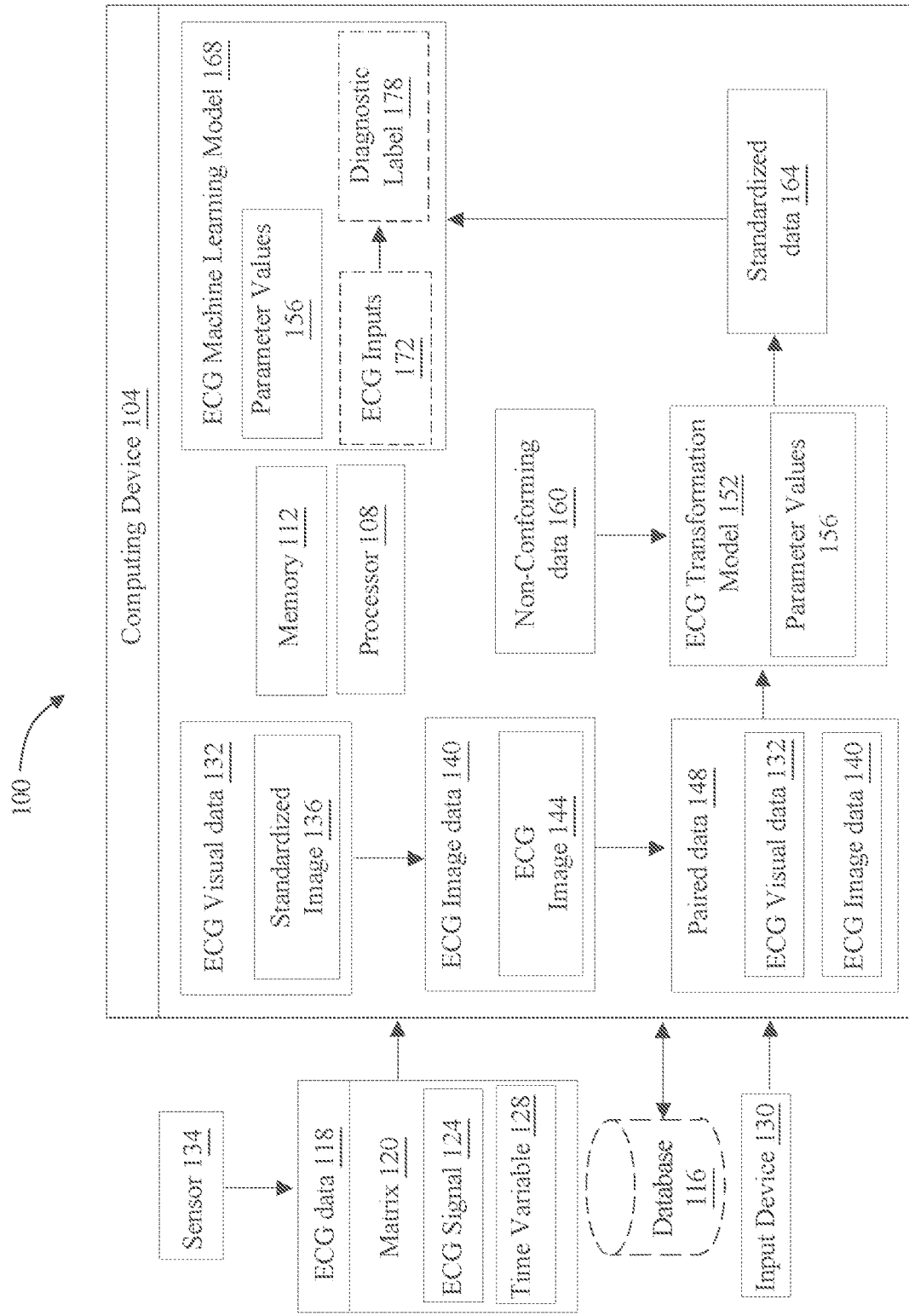
FIG. 1 is an exemplary embodiment of a system for transforming electrocardiogram images for use in one or more machine learning models.

Referring now to FIG. 1, a system 100 for training machine learning models using unlabeled electrocardiogram data is described. System 100 includes a computing device 104. System 100 includes a processor 108. Processor 108 may include, without limitation, any processor 108 described in this disclosure. Processor 108 may be included in a and/or consistent with computing device 104. In one or more embodiments, processor 108 may include a multi-core processor. In one or more embodiments, multi-core processor may include multiple processor cores and/or individual processing units. "Processing unit" for the purposes of this disclosure is a device that is capable of executing instructions and performing calculations for a computing device 104. In one or more embodiments, processing units may retrieve instructions from a memory, decode the data, secure functions and transmit the functions back to the memory. In one or more embodiments, processing units may include an arithmetic logic unit (ALU) wherein the ALU is responsible for carrying out arithmetic and logical operations. This may include, addition, subtraction, multiplication, comparing two data, contrasting two data and the like. In one or more embodiments, processing unit may include a control unit wherein the control unit manages execution of instructions such that they are performed in the correct order. In none or more embodiments, processing unit may include registers wherein the registers may be used for temporary storage of data such as inputs fed into the processor and/or outputs executed by the processor. In one or more embodiments, processing unit may include cache memory wherein memory may be retrieved from cache memory for retrieval of data. In one or more embodiments, processing unit may include a clock register wherein the clock register is configured to synchronize the processor with other computing components. In one or more embodiments, processor 108 may include more than one processing unit having at least one or more arithmetic and logic units (ALUs) with hardware components that may perform arithmetic and logic operations. Processing units may further include registers to hold operands and results, as well as potentially "reservation station" queues of registers, registers to store interim results in multi-cycle operations, and an instruction unit/control circuit (including e.g. a finite state machine and/or multiplexor) that reads op codes from program instruction register banks and/or receives those op codes and enables registers/arithmetic and logic operators to read/output values. In one or more embodiments, processing unit may include a floating-point unit (FPU) wherein the FPU is configured to handle arithmetic operations with floating point numbers. In one or more embodiments, processor 108 may include a plurality of processing units wherein each processing unit may be configured for a particular task and/or function. In one or more embodiments, each core within multi-core processor may function independently. In one or more embodiments, each core within multi-core processor may perform functions in parallel with other cores. In one or more embodiments, multi-core processor may allow for a dedicated core for each program and/or software running on a computing system. In one or more embodiments, multiple cores may be used for a singular function and/or multiple functions. In one or more embodiments, multi-core processor may allow for a computing system to perform differing functions in parallel. In one or more embodiments, processor 108 may include a plurality of multi-core processors. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing devices operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory 112 between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a Processor module to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, system 100 includes a memory 112 communicatively connected to processor 108, wherein the memory 112 contains instructions configuring processor 108 to perform any processing steps as described herein. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 112 may include a primary memory and a secondary memory. "Primary memory" also known as "random access memory" (RAM) for the purposes of this disclosure is a short-term storage device in which information is processed. In one or more embodiments, during use of computing device 104, instructions and/or information may be transmitted to primary memory wherein information may be processed. In one or more embodiments, information may only be populated within primary memory while a particular software is running. In one or more embodiments, information within primary memory is wiped and/or removed after computing device 104 has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 108 may access the information from primary memory.

Still referring to FIG. 1, System 100 may include a database 116. Database may include a remote database 116. Database 116 may be implemented, without limitation, as a relational database, a key-value retrieval database such as a NOSQL database, or any other format or structure for use as database that a person skilled in the art would recognize as suitable upon review of the entirety of this disclosure. Database may alternatively or additionally be implemented using a distributed data storage protocol and/or data structure, such as a distributed hash table or the like. Database 116 may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments. In one or more embodiments, computing device 104 may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by system computing device 104. In one or more embodiments, computing device 104 may transmit processes to server wherein computing device 104 may conserve power or energy.

With continued reference to FIG. 1, processor 108 may be configured to receive electrocardiogram data 118. "Electrocardiogram data" for the purposes of this disclosure is information associated with electrocardiogram signals. In one or more embodiments, electrocardiogram data 118 may include a matrix 120 having a plurality of electrocardiogram signals 124 and/or associated time variables 128. A "matrix" for the purposes of this disclosure is an array of numbers or characters arranged in rows or columns which are used to represent an object or properties of the object. For example, and without limitation, a matrix may be used to describe linear equations, differential equations, in a two-dimensional format. In another non limiting example, a matrix may be used to create graphs based on data points, generate statistical models and the like. In one or more embodiments, matrix 120 may include a plurality of electrocardiogram signals associated with a plurality of time variables 128. As used in the current disclosure, a "electrocardiogram signal" is a signal representative of electrical activity of heart. The ECG signal 124 may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves may provide information about the duration and regularity of various phases of the cardiac cycle. The ECG signal 124 may help diagnose various heart conditions, such as arrhythmias, myocardial infarction (heart attack), conduction abnormalities, and electrolyte imbalances. In one or more embodiments, ECG signals 124 may be received by one or more electrodes connected to the skin of an individual. In one or more embodiments, ECG signals 124 may represent depolarization and repolarization occurring in the heart. In one or more embodiments, ECG signals 124 may be captured periodically. For example, and without limitation, every second, every millisecond and the like. In one or more embodiments, each ECG signal 124 may contain an associated time variable 128. "Time variable" for the purposes of this disclosure is information indicating the time at which a particular ECG signal 124 was received. For example, and without limitation, time variable 128 may include, 5 ms, 10 ms, 15 ms and the like. In one or more embodiments, each ECG signal 124 may contain a time variable 128. In one or more embodiments, time variable 128 may increase in given increments, such as for example, in increments of 5 ms, wherein a first time variable 128 may include 5 ms and a second time variable 128 may include 10 ms. In one or more embodiments, a combination of a plurality of ECG signals 124 and correlated time variable 128 may be used to generate a graph illustrating the heart functions of an individual. In one or more embodiments, matrix 120 may include a plurality of ECG signals 124 and correlated time variable 128 during a given time frame such as, for example, over the span of a second, a minute, an hour, and the like. In one or more embodiments, ECG signals 124 may be captured as voltages, such as millivolts or microvolts.

With continued reference to FIG. 1, the plurality of electrocardiogram signals may capture a temporal view of cardiac electrical activities. A "temporal view," as used in the current disclosure, refers to the analysis and visualization of heart-related events and phenomena over time. A temporal view may include patterns, changes, and dynamics of cardiac activity over time. A temporal view may include information surrounding the rhythm of the heart, including the regularity or irregularity of heartbeats. It allows for the identification of various rhythm abnormalities such as tachycardia (fast heart rate), bradycardia (slow heart rate), or arrhythmias (irregular heart rhythms). A temporal view of cardiac activities in three dimensions may refer to a visualization that represents the temporal evolution of cardiac events or phenomena in a three-dimensional space. It provides a comprehensive understanding of how various cardiac activities change over time. The ECG signal 124 may move through the 3D space of the heart over time. The signal does not just move forward in time, it also moves through the physical space of the heart, from SA node through atria, to AV node, and then through the ventricles. Such movement of the electrical signal through the heart's physical space over time can be referred to as "spatiotemporal excitation and propagation" which could be captured by plurality of ECG signals 124. It is essentially a way of observing and analyzing the timing and sequence of the heart's electrical activity as it moves through the physical structure of the heart. In the current case the dimensions may include axis representing time, spatial dimensions, and cardiac activity. By combining the temporal, spatial, and cardiac activity dimensions, the temporal view of cardiac activities in three dimensions allows for a comprehensive visualization and analysis of dynamic changes occurring within the heart. It can be used to study phenomena like electrical conduction, ventricular wall motion, valve function, blood flow dynamics, or the interaction between different regions of the heart. This visualization approach provides valuable insights into the complex temporal dynamics of cardiac activities and aids in understanding cardiac function, pathology, and treatment evaluation.

With continued reference to FIG. 1, matrix 120 and/or ECG signals 124 may be received through one or more input devices 130. "Input device" for the purposes of this disclosure is a device capable of transmitting information to computing device. For example, and without limitation, input device 130 may include a keyboard, a mouse, a touchscreen, a smartphone, a network server, a sensor 134 and the like. In one or more embodiments, input device 130 may include a sensor 134. In one or more embodiments, matrix 120 and/or ECG signals 124 may be received by input device 130 and/or sensor 134. As used in this disclosure, a "sensor" is a device that is configured to detect an input and/or a phenomenon and transmit information related to the detection. Sensor 134 may detect a plurality of data. A plurality of data detected by sensor 134 may include, but is not limited to, electrocardiogram signals, heart rate, blood pressure, electrical signals related to the heart, time variables 128 associated with captured data and the like. In one or more embodiments, and without limitation, sensor 134 may include a plurality of sensors 134. In one or more embodiments, and without limitation, sensor 134 may include one or more electrodes, and the like. Electrodes used for an electrocardiogram (ECG) are small sensors 134 or conductive patches that are placed on specific locations on the body to detect and record the electrical signals generated by the heart. Senor may serve as the interface between the body and the ECG machine, allowing for the measurement and recording of the heart's electrical activity. A plurality of sensors 134 may include 10 electrodes used for a standard 12-lead ECG, placed in specific positions on the chest and limbs of the patient. These electrodes are typically made of a conductive material, such as metal or carbon, and are connected to lead wires that transmit the electrical signals to the ECG machine for recording. In one or more embodiments, plurality of ECG signals 124 may be associated with a 12-lead electrocardiogram. Proper electrode placement is crucial to ensure accurate signal detection and recording. In one or more embodiments, sensors 134 may include wireless sensors 134 wherein data may be received from sensor 134 to computing device wirelessly. In one or more embodiments, wireless sensors 134 may include Bluetooth enabled ECG sensors, RFID ECG sensors, Wi-Fi enabled ECG sensors and the like. In one or more embodiments, wireless sensors 134 may allow for receipt of data from a distance. In one or more embodiments, wireless sensors 134 may allow for a machine or system to receive data without wires connecting the sensors 134 to computing device. In one or more embodiments, the presence of wires from sensors 134 to computing device may obstruct medical personnel from conducting one or more medical treatment procedures.

With continued reference to FIG. 1, the plurality of sensors 134 may be placed on each limb, wherein there may be at least one sensor on each arm and leg. These sensors may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line. In one or more embodiments, each sensor and/or lead may contain a set of electrical signals, wherein matrix 120 may include ECG signals 124 associated with each lead and/or sensor.

With continued reference to FIG. 1, the plurality of sensors may include augmented unipolar sensors. These sensors may be labeled as aVR, aVL, and aVF. These sensors may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions. These leads capture the electrical signals from different orientations, which are then transformed into transformed coordinates to generate vectorcardiogram (VCG) representing magnitude and direction of electrical vectors during cardiac depolarization and repolarization. Transformed coordinates may include one or more a Cartesian coordinate system (x, y, z), polar coordinate system (r, $\theta$), cylindrical coordinate system ($\rho$, $\varphi$, z), or spherical coordinate system (r, $\theta$, $\varphi$). In some cases, transformed coordinates may include an angle, such as with polar coordinates, cylindrical coordinates, and spherical coordinates. In some cases, VCG may be normalized thus permitting full representation with only angles, i.e., angle traversals. In some cases, angle traversals may be advantageously processed with one or more processes, such as those described below and/or spectral analysis.

With continued reference to FIG. 1, in one or more embodiments, sensor 134 may include surface electrodes wherein the surface electrodes may be placed above the skin of a user and used to detect electrical impulses. In one or more embodiments, sensor 134 may further include a wearable ECG monitor wherein the wearable ECG monitor may be wrapped around a limb of the individual and used to detect electrical impulses. In one or more embodiments, sensor 134 may further include a Holter monitor, subdermal needle electrodes, and/or any other sensing device capable of receiving electrical signals.

With continued reference to FIG. 1, matrix 120 may include a plurality of ECG signals 124 captured at discrete time intervals. In one or more embodiments, matrix 120 may be generated and/or received in a digital imaging and communications in medicine (DICOM) Format, a CSV format, as a spread sheet containing cells for each datum and the like. In one or more embodiments, computing device may receive data in a raw format wherein the data may be converted into a matrix.

With continued reference to FIG. 1, ECG signals 124 received from each sensor 134 may be referred to as an 'ECG set.' In one or more embodiments, an ECG set may include ECG signals 124 captured from a singular sensor 134 over a given period of time. In one or more embodiments, ECG data 118 may include a plurality of ECG sets wherein each ECG sets may correspond to a differing input device differing sensor 134 and the like in contact with an individual. In one or more embodiments, each ECG set may correspond to a different surface electrode in contact with an individual. In one or more embodiments, ECG data 118 may include ECG sets wherein ECG sets include similar timeframes in which ECG signals 124 are captured. For example, and without limitation, an 8-lead system 100 may include 8 ECG sets wherein each ECG set corresponds to a particular lead.

With continued reference to FIG. 1, processor 108 may be configured to receive plurality of ECG data 118. In one or more embodiments, ECG data 118 may be received in textual format. A "Textual format" for the purposes of this disclosure is a format in which a set of data is represented by characters, numbers or any other alphanumeric representations. For example, and without limitation, a set of data may be said to be in textual format in instances in which the contents of the file contain only characters of readable material. In one or more embodiments, data in textual format may be contrasted with an image, video and the like. In one or more embodiments, data within a textual format may include machine-readable alphanumeric characters. In one or more embodiments, data within a textual format may include data such as .txt, .docx, .xlsx and the like. In one or more embodiments, ECG data 118 may be received in textual format wherein ECG data 118 may include textual data corresponding to Leads and corresponding voltage signals of the leads.

In one or more embodiments, ECG data 118 may include matrix 120 and/or an array of data wherein matrix 120 may include matrix 120 of size N×T, where N is the number of leads in the ECG and T is the number of voltage signals recorded in that ECG. In one or more embodiments, 'T' will depend on the frequency of the acquired ECG data 118 (referred to herein as 'f') and the length of the signal in seconds (referred to herein as 's'), i.e., T=f*S. In one or more embodiments, matrix 120 may include a two dimensional array having size of N×T wherein N may denote the number and/or particular leads and T may denote the voltage signals. In one or more embodiments, ECG data 118 may be received in a 3-dimesnional array of N×T×S wherein s may denote the seconds and/or time corresponding to each voltage signal. In one or more embodiments, ECG data 118 may include a matrix 120 having one or more leads and voltage signals associated with each of the one or more leads. In an embodiment, each lead may be configured to receive voltage signals from a patient wherein ECG data 118 may include voltage signals from each lead on the patient. In one or more embodiments, leads may include any leads as described above. In one or more embodiments, each ECG data 118 may include data received from multiple leads in contact with a patient. In one or more embodiments, processor 108 may be configured to receive a plurality of ECG data 118 wherein each ECG data 118 is associated with a particular individual and/or medical patient. In one or more embodiments, ECG data 118 may contain voltage signals over a given period of time and/or ECG signals 124. In one or more embodiments, each voltage signal within ECG data 118 may contain corresponding time variable 128 (as described above) wherein time variable 128 denotes the time at which the particular voltage signal was received. In an embodiment, matrix 120 may include an array for each lead wherein the array contains voltage signals and time variables 128 associated with the voltage signals. In one or more embodiments, sensors 134 associated with each lead may be configured to receive voltage signals and corresponding time variables 128. In one or more embodiments, ECG data 118 may be received from a plurality of patients, from a database 116, from a web using a web crawler and the like. In one or more embodiments, each set of ECG data 118 may correspond to a particular individual and/or patient. In one or more embodiments, ECG data 118 may contain ECG signals 124 received from each sensor 134 of a plurality of sensors 134 that were in contact with a patient. In one or more embodiments, the sensors 134 may be configured to receive ECG signals 124 and associated time variables 128 denoting the time at which the ECG signal 124 was received. In one or more embodiments, ECG signals 124 may be received from an 8 or lead ECG wherein each lead includes a sensor 134 configured to receive ECG signals 124 from a particular portion of an individual's body. In one or more embodiments, ECG data 118 may contain ECG signals 124 from multiple electrodes recorded over a similar time frame. For example, and without limitation, ECG data 118 may include ECG signals 124 received from multiple electrodes over a similar timeframe of 0 to 10 seconds.

With continued reference to FIG. 1, processor 108 is configured to generate ECG visual data 132 as a function of ECG data 118. "ECG visual data" for the purposes of this disclosure is a computer generated graphical representation of the electrocardiogram signals recorded within ECG data 118. For example, and without limitation, ECG visual data 132 may include a two dimensional X-y chart wherein electrocardiogram signals are plotted over a given time. In one or more embodiments, ECG signals 124 may be plotted along a vertical axis whereas corresponding time variables 128 may be plotted along a horizontal axis. In one or more embodiments, ECG visual data 132 may include computer generated images of plotted ECG signals 124 and corresponding time variables 128. In one or more embodiments, each ECG set may be plotted individually. In one or more embodiments, multiple ECG sets associated with the same individual may be plotted on a singular chart or graph. In one or more embodiments, processor 108 may be configured to receive ECG data 118 and generate ECG visual data 132. In one or more embodiments, processor 108 may be configured to generate a graphical representation of each ECG signal 124 and/or set of ECG signals 124. In one or more embodiments, graphical representation may include an ECG waveform wherein the waveform includes a graphical representation of ECG data 118. In one or more embodiments, Time may be shown along a horizontal and/or X axis while ECG signals 124 (i.e. voltage) may be shown along the vertical and/or Y axis.

With continued reference to FIG. 1, in one or more embodiments, ECG visual data 132 includes a plurality of standardized images 136. A "standardized image" for the purposes of this disclosure in an image that adheres to a particular set of rules or standards. For example, and without limitation, a set of rules or standards may indicate that an image may only contain a size ratio of 8.5×11 and must be in a PDF format wherein standardized image 136 may be 8.5×11 and in a pdf format. In one or more embodiments, plurality of standardized images 136 include images with similar file types, similar size ratios, similar contrast, similar brightness and the like. In one or more embodiments, standardized images 136 may include images that have been captured in a similar manner, such as for example, with a similar camera, scanning device, similar resolution and the like. In one or more embodiments, ECG visual data 132 may contain a plurality of standardized images 136 wherein the computer generated images are all generated in a similar manner. In one or more embodiments, Standardized images 136 may include in-silicon quality images. An "in-silicon quality image" for the purposes of this disclosure is an image generated from silicon based technologies or a computer environment. In one or more embodiments, In-silicon quality images may be generated by simulations, computer graphics, digital imaging processes and the like. In one or more embodiments, in-silicon quality image may include a graphical representation of ECG signals 124 produced through computational methods by converting ECG signals 124 into visual graphics. In one or more embodiments, the images would depict waveform patterns and characteristics of the ECG signals 124. In one or more embodiments, processor 108 may generate in-silicon quality image through the creation of spectrograms, wavelet transformation techniques and the like. In one or more embodiments, standardized images 136 may include images with similar quality, resolution, contrast, and the like, wherein images of ECG signals 124 may be generated with similar quality.

With continued reference to FIG. 1, standardized images 136 may be generated in various layouts, wherein multipole ECG sets associated with the same patient may be placed within a single standardized image 136. In one or more embodiments, processor 108 may use software configured for plotting, such as Matlab, Plotly, Seaborn, Bokeh and the like. In one or more embodiments, standardized images 136 may be generated in varying layouts wherein each layout may contain differing sets of ECG signals 124. IN one or more embodiments, layouts may include but are not limited 3×4 (3 leads placed across four rows), 3×4 with 1 Rhythm lead (3 leads placed across 4 rows with one additional lead dedicated to displaying rhythm), 6×2 (6 leads placed across two rows), 6×2 with 1 Rhythm lead (6 leads placed across two rows with 1 rhythm lead), 12×1, 3×4 with 2 rhythm leads, 3×4 with 3 rhythm leads (3 leads placed across 4 rows with three rhythm leads), Pan 12 layout and the like. In one or more embodiments, multiple leads and multiple rows may be placed within the same standardized image 136. In one or more embodiments, standardized images 136 may contain differing layouts but similar quality, color contrast, and the like. In one or more embodiments, standardized images 136 may further contain differing settings for generating graphical representation of ECG signals 124. In one or more embodiments, differing settings may include but are not limited to, paper speeds of 25 mm/s or 50 mm/s, with limb lead scale of 2.5 mm/mV, 5 mm/mV, 10 mm/mV, 20 mm/mV, with full scale chest leads and half scale chest leads. Time sequential versus Simultaneous, Standard and Cabrera format and the like. In one or more embodiments differing settings may further include with reference signal at end, or with reference signal at start or no reference signal, with a separator between lead signals or without separator between lead signals and the like. In an embodiments, Graphical representations of ECG signals 124 may differ with respect to layouts of the ECG signals 124, layouts of the rhythms, differing paper speeds and the like. In one or more embodiments, generating ECG visual data 132 may include plotting ECG data 118.

With continued reference to FIG. 1, processor 108 may be configured to receive ECG image data 140 comprising a plurality of ECG images 144 associated with ECG data 118. An "ECG image" for the purposes of this disclosure is a graphical or visual representation of electrocardiogram signals depicted as a photographic or scanned image. For example, and without limitation, ECG image may include a photograph of ECG signals, a chart of ECG signals on a paper that has been scanned and the like. In one or more embodiments, ECG image 144 may include a two dimensional plot in which electrocardiogram signals are graphed over a given period of time. In one or more embodiments, ECG image 144 may include a scanned image of an electrocardiogram plot. In one or more embodiments, ECG image data 140 may include images scanned physical documents and/or data that has been given the appearance of a scanned physical document. For example, and without limitation, ECG image data 140 may include images received from a scanner, images received from a camera, images received from a scanning device and the like. In one or more embodiments, ECG image data 140 may include a digitized version of image captured from various sources such as a camera and/or any other input devices. In one or more embodiments, ECG image data 140 may include digitized paper prints. In one or more or more embodiments, different printers may create paper ECG in different ECG layouts as mentioned above. In one or more embodiments, printers may include but are not limited to, Thermal printers, Laser printers, Inkjet printers, Ink-tank printers, Dot-matrix printers and the like. In one or more embodiments, computing device 104 and/or a separate computing system may be used to print ECG signals 124 in graphical format using a variety of printers. In one or more embodiments, images may be black and white, color, have varying brightness, have varying contrast and the like. In one or more embodiments, paper prints may also be generated by printing via an ECG device by feeding in raw voltage-time series data. The ECG prints received from the ECG device may be similar to those found in clinical settings. Paper prints may also be generated by taking a printout of PDF version of the ECG similar to setup shown in FIG. 1 except that instead of printing to ECG machine printer—it would be saved as PDF in ECG machine and would be exported out and printed in various layouts using one of the printers mentioned above. In one or more embodiments, standardized images 136 generated by processor 108 may be printed in a physical forma through a variety of printers and rescanned through one or more inputs devices back into a digitized form. In one or more embodiments, physical prints may be rescanned using inputs devices such as but not limited to, mobile phone cameras, scanners with differing qualities and DPIs, standalone cameras, taking a screenshot from a screen, taking a screenshot from a photo, Taking a screenshot of an ECG signal 124 in an ECG viewer software and the like. In one or more embodiments, processor 108 may be configured to simulate a process of printing standardized images 136 and rescanning them. In one or more embodiments, processor 108 may be configured to simulate printing and scanning processes by adjusting the resolution of images, adjusting the DPI of images, adjusting the brightness of images, varying the color of images, varying the format of various images, simulating paper creases similar to that in a scanned image, simulating light obstructions in the images and the like. In one or more embodiments, processor 108 may generate ECG image data 140 by receiving ECG visual data 132 and simulating one or more processes of printing and scanning a standardized image 136 within ECG visual data 132. In one or more embodiments, ECG image data 140 may contain a plurality of non-conforming images. A "non-conforming image" for the purposes of this disclosure is an image differing in quality, format, and the like in comparison to other images. In one or more embodiments, ECG image data 140 may contain a plurality of nonconforming images wherein images may contain differing light intensities, differing resolutions, differing formats and the like. In one or more processor 108 may be configured to simulate a plurality of input devices wherein images within ECG image data 140 may vary in brightness, contrast, size and the like. In one or more embodiments, each image within ECG image data 140 may be correlated to ECG signals 124 within ECG data 118 and/or correlated with standardized image 136 within ECG visual data 132.

With continued reference to FIG. 1, processor 108 is configured to receive paired data 148. "Paired data" for the purposes of this disclosure is training data that may be used to train one or more machine learning models. In one or more embodiments, paired data 148 may include inputs the machine learning model is expected to receive and outputs the machine learning model is configured to generate. Training data and machine learning models is described in further detail below. In one or more embodiments, paired data 148 may include plurality of ECG images 144 correlated to a plurality of standardized images 136. In one or more embodiments, paired data 148 includes ECG visual data 132 and ECG image data 140. In one or more embodiments, ECG visual data 132 and ECG image data 140 may be correlated wherein each ECG image 144 within ECG image data 140 may be correlated to each standardized image 136 of ECG visual data 132. In one or more embodiments, ECG image data 140 may include inputs to the machine learning model and ECG visual data 132 may contain correlated outputs to the machine learning model. In one or more embodiments, paired data 148 may include ECG image data 140 and correlated ECG visual data 132, wherein each ECG image 144 within ECG image data 140 may contain a correlated standardized image 136. In an embodiment, each ECG image 144 may contain a set of ECG signals 124, wherein each standardized image 136 may contain the same set of ECG signals 124 in a standardized format. In one or more embodiments, each ECG image 144 and correlated standardized image 136 may depict similar information yet differ in image quality, brightness and the like. In one or more embodiments, each ECG image 144 and correlated standardized image 136 may contain similar settings and layouts with respect to the graphical representation of ECG signals 124 yet vary in quality, format, and the like.

With continued reference to FIG. 1, paired data 148 may include augmented images. In one or more embodiments, an augmented image may include an image that has been altered from its original form such that a portion of the image is now masked or missing. For example, and without limitation, Augmented image may include an image that has been cropped from its original size, an image that been split into two and the like. In one or more embodiments, paired data 148 may include augmented images. In one or more embodiments, ECG images 144 within ECG image data 140 may be augmented wherein portions of ECG images 144 are obscured, removed and the like. In one or more embodiments, processor 108 may augment images within ECG image data 140 at random. In one or more embodiments, processor 108 may receive a set of correlated images from ECG image data 140 and ECG visual data 132 and augment the image within ECG image data 140. In one or more embodiments, augmentation of images within paired data 148 may allow for training of one or more machine learning models as described below. In one or more embodiments, paired data 148 may include plurality of ECG images 144 correlated to plurality of standardized images 136, wherein each ECG image 144 of plurality of ECG images 144 is correlated with each standardized image 136 of plurality of standardized images 136. In one or more embodiments, paired data 148 may be received as described above. In one or more embodiments, paired data 148 may further be received through user inputs, from a database 116 and the like.

With continued reference to FIG. 1, processor 108 is configured to train an ECG transformation model 152 as a function of paired data 148. An "ECG transformation model" as described herein is a system configured to receive non-conforming images as inputs and output standardized images 136. In one or more embodiments, ECG transformation model 152 may receive images of ECG signals 124 and transform the images into clear images adhering to a particular set of rules. For example, and without limitation, ECG transformation model 152 may be configured to receive an image of an ECG signal 124 that has been received from a scanning device and output or generate an in-silicon image. In one or more embodiments, ECG transformation model 152 may include a machine learning model configured to receive inputs such as ECG image data 140 and output ECG visual data 132. In one or more embodiments, ECG transformation model 152 may be configured to receive images varying from differing sources and transform the images to a similar format in comparison to one another. In one or more embodiments, computing device 104 may include a machine learning module to implement one or more algorithms or generate one or more machine-learning models to generate outputs. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from database 116, user inputs and/or be provided by a user. In other embodiments, a machine-learning module may obtain a training set by querying a communicatively connected database 116 that includes past inputs and outputs. Training data may include inputs from various types of databases 116, resources, libraries, dependencies and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to categories by tags, tokens, or other data elements. A machine learning module may be used to create a machine learning model and/or any other machine learning model using training data. Training data may be data sets that have already been converted from raw data whether manually, by machine, or any other method. In some cases, the machine learning model may be trained based on user input. For example, a user may indicate that information that has been output is inaccurate wherein the machine learning model may be trained as a function of the user input. In some cases, the machine learning model may allow for improvements to computing device 104 such as but not limited to improvements relating to comparing data items, the ability to sort efficiently, an increase in accuracy of analytical methods and the like.

With continued reference to FIG. 1, in one or more embodiments, a machine-learning module may be generated using training data. Training data may include inputs and corresponding predetermined outputs so that machine-learning module may use the correlations between the provided exemplary inputs and outputs to develop an algorithm and/or relationship that then allows machine-learning module to determine its own outputs for inputs. Training data may contain correlations that a machine-learning process may use to model relationships between two or more categories of data elements. The exemplary inputs and outputs may come from a database 116, and/or be provided by a user. In other embodiments, machine-learning module may obtain a training set by querying a communicatively connected database 116 that includes past inputs and outputs. Training data may include inputs from various types of databases 116, resources, libraries, dependencies and/or user inputs and outputs correlated to each of those inputs so that a machine-learning module may determine an output. Correlations may indicate causative and/or predictive links between data, which may be modeled as relationships, such as mathematical relationships, by machine-learning processes, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. In one or more embodiments, ECG transformation model 152 may include a machine learning model configured to receive inputs similar to that of ECG image data 140 and output standardized images 136 similar to that of ECG visual data 132.

With continued reference to FIG. 1, paired data 148 may be used to train ECG transformation model 152. In one or more embodiments, paired data 148 may include ECG image data 140 correlated to ECG visual data 132. In one or more embodiments, paired data 148 may be used to train ECG transformation model 152 wherein transformation model may be configured to receive inputs and generate outputs in a standardized format.

With continued reference to FIG. 1, training ECG transformation model 152 may include a process in which ECG transformation model 152 and/or processor 108 may predict standardized images 136 and/or ECG visual data 132 from ECG image data 140. For example, and without limitation, ECG transformation model 152 may receive an ECG image 144 from without ECG image data 140 and predict the correlating standardized image 136. In one or more embodiments ECG transformation model 152 may compare predictions to the actual information contained within ECG visual data 132. In one or more embodiments, ECG transformation model 152 may be configured to receive ECG image data 140 and/or portions thereof wherein ECG transformation model 152 may be tasked with predicting correlated standardized images 136. In one or more embodiments, ECG transformation model 152 may be configured with a pretext task. In one or more embodiments, the pretext task may include predicting and/or finding standardized images 136. In one or more embodiments, ECG transformation model 152 may extract relevant features from ECG image data 140 in order to predict ECG visual data 132. In one or more embodiments, ECG transformation model 152 may contain a predetermined set of values of parameters wherein the parameters refer to weights and biases. In one or more embodiments, parameters may be initialized randomly or received from similar machine learning models. In one or more embodiments, during training, parameters of ECG transformation model 152 may be given initial values wherein the parameters may change in order to fine tune machine learning model for a specific purpose. In one or more embodiments, training involves modifying parameters based on the input data and correlated output data in order to learn meaningful representations or features that can be further refined further on in order fine tune ECG transformation model 152. In one or more embodiments, ECG transformation model 152 may receive as an input ECG image data 140 and predict visual data. In one or more embodiments, ECG transformation model 152 may compare predictions of ECG visual data 132 to actual ECG visual data 132. In one or more embodiments, ECG transformation model 152 may utilize a loss function in order to measure the discrepancy between predicted outputs of ECG transformation model 152 and the actual outputs. In one or more embodiments, ECG transformation model 152 may adjust parameters iteratively through optimization techniques such as, but not limited to gradient descent to minimize the discrepancy.

In one or more embodiments, a machine learning model such as ECG transformation model 152 may contain parameter values 156. "Parameter values" for the purposes of this disclosure are internal variables that a machine learning model has generated from training data in order to make predictions. In one or more embodiments, parameter values 156 may be adjusted during pretraining or training in order to minimize a loss function. In one or more embodiments, during training, predicted outputs of the machine learning model are compared to actual outputs wherein the discrepancy between predicted output and actual outputs are measured in order to minimize a loss function. A loss function also known an "error function" may measure the difference between predicted outputs and actual outputs in order to improve the performance of the machine learning model. A loss function may quantify the error margin between a predicted output and an actual output wherein the error margin may be sought to be minimized during the training process. The loss function may allow for minimization of discrepancies between predicted outputs and actual outputs of the machine learning model. In one or more embodiments, the loss function may adjust parameter values 156 of the machine learning model. In one or more embodiments, in a linear regression model, parameter values 156 may include coefficients assigned to each feature and the bias term. In one or more embodiments, in a neural network, parameter values 156 may include weights and biases associated with the connection between neurons or nodes within layers of the network. In one or more embodiments, during pretraining and/or training of the machine learning model, parameter values 156 of the machine learning model (e.g. ECG transformation model 152) may be adjusted as a function of at least one predicted standardized image 136 within ECG visual data 132 and the actual standardized image 136. In one or more embodiments, processor 108 may be configured to minimize a loss function by adjusting parameter values 156 of ECG transformation model 152 based on discrepancies between predicted outputs and actual outputs as indicated with ECG visual data 132. In one or more embodiments, training ECG transformation model 152 may include adjusting one or more parameter values 156 of ECG transformation model 152 as a function of a comparison between at least one predicted standardized image 136 and at least one standardized image 136 of the plurality of standardized images 136 within ECG visual data 132. In one or more embodiments, processor 108 may be configured to iteratively train ECG transformation model 152, wherein processor 108 may be configured to iteratively receive ECG signals 124 from patients, paired data 148 and/or the like and adjust parameter values 156 of ECG transformation model 152. In an embodiment, the more ECG data 118 and/or paired data 148 received by ECG transformation model 152, the more accurate the ECG transformation model 152 may be in predicting standardized images 136. In one or more embodiments, parameter values 156 may correspond to learned features of paired data 148 such as waveforms, patterns, frequencies and the like.

With continued reference to FIG. 1, processor 108 is configured to receive non-conforming data 160. In one or more embodiments, processor 108 is configured to receive non-conforming data 160 for use in ECG transformation model 152. "Non-conforming data" for the purposes of this disclosure refers to images of ECG signals 124 associated with patients that do not conform to a predetermined set of rules or standards. In an embodiments, non-conforming data 160 may include images similar to that of ECG images 144. In an embodiments, ECG images 144 may be used to train ECG transformation model 152 whereas non-conforming data 160 may be used to receive images which have been standardized. In one or more embodiments, non-conforming data 160 may include images of ECG signals 124 received from mobile devices, printouts, scanned physical documents, and the like. In one or more embodiments, non-conforming data 160 may include images that have varying quality, varying orientations, differing color contrast, differing dots per inch and the like. In one or more embodiments, non-conforming data 160 may contain issues with light reflections, exposure issues, and the like. In one or more embodiments, non-conforming data 160 may include images that have been unintentionally cropped or are missing portions of the image. In one or more embodiments, non-conforming data 160 may include ECG images 144 that have not been used for training of ECG transformation model 152. In one or more embodiments, non-conforming data 160 may be received from a user of system 100, by querying database 116 and the like. In one or more embodiments, non-conforming data 160 may be received by a web crawler. A "web crawler," as used herein, is a program that systematically browses the internet for the purpose of web indexing. Web crawler may be seeded with platform URLs, wherein the crawler may then visit the next related URL, retrieve the content, index the content, and/or measures the relevance of the content to the topic of interest. In some embodiments, computing device 104 may generate a web crawler to compile and/or generate a plurality of requirements and/or elements thereof. The web crawler may be seeded and/or trained with a reputable website, such as governmental websites, medical websites, research websites associated with medical research and the like. Web crawler may be generated by computing device 104. In some embodiments, the web crawler may be trained with information received from a user through a user interface. In some embodiments, the web crawler may be configured to generate a web query. A web query may include search criteria received from a user. For example, a user may submit a plurality of websites for the web crawler to search to extract any data suitable for the plurality of requirements. In one or more embodiments, non-conforming data 160 may be received iteratively by a web crawler. In one or more embodiments, the larger the amount of data received, the more accurate a machine learning model may be as described in further detail below. In one or more embodiments, processor 108 may be configured to iteratively and/or periodically configure web crawler to retrieve non-conforming data 160 wherein non-conforming data 160 may be fed to ECG transformation model 152.

With continued reference to FIG. 1, ECG transformation model 152 is configured to output standardized data 164 as a function of non-conforming data 160. "Standardized data" for the purposes of this disclosure is a data set containing standardized images 136. In an embodiments, ECG transformation model 152 may be configured to receive non-conforming data 160 wherein images within non-conforming data 160 may be converted to a particular standardized format. In one or more embodiments, Standardized data 164 may contain in-silicon quality images generated from images within non-conforming data 160. In one or more embodiments, ECG transformation model 152 may output a computer generated image adhering to a particular set of rules or standards for each image within conforming data. In one or more embodiments, ECG transformation model 152 may be configured to generate standardized data 164 wherein the images within standardized data 164 may be similar to images within ECG visual data 132. In one or more embodiments, following training, ECG transformation model 152 may be configured to generate standardized data 164.

With continued reference to FIG. 1, standardized data 164 may be used as and/or include unlabeled training data. "Unlabeled training data" for the purposes of this disclosure is data that lacks distinct elements or classifiers that can be used to train a machine learning model. In an embodiment, unlabeled training data may include data that has not been classified by an individual or computing system. In one or more embodiments, "labeled training data" may refer to data that has been labeled and configured to training machine learning models. in an embodiment, labeled training data may include training data with inputs and correlated outputs. In an embodiment, paired data 148 may include labeled training data wherein paired data 148 includes inputs such as EXCG images data and correlated outputs such as ECG visual data 132. In an embodiment, unlabeled training data may include data that has not been modified to train machine learning models. In one or more embodiments, unlabeled training data may include data that may be used for training of one or more machine learning models but has not been specifically modified for the training of one or more machine learning models. In one or more embodiments, unlabeled training data may lack tags, labels, classifications, correlated outputs and the like. In one or more embodiments, standardized data 164 may contain unlabeled training data. In one or more embodiments, Standardized data 164 may include any training data as described in this disclosure. In one or more embodiments, standardized training data may become iteratively larger following each iterations of the processing. In one or more embodiments, standardized data 164 may become iteratively larger through additional non-conforming data 160 received through web crawlers, user input and the like.

With continued reference to FIG. 1, standardized data 164 may be used for multiple downstream tasks. As used in this disclosure downstream tasks may refer to machine learning models that utilize ECG signals for differing purposes Multiple downstream task models may be trained using ECG Images/extracted ECG signal from images. In one or more embodiments, Downstream task models may utilize standardized data to train or pretrain the machine learning models for differing purposes. The downstream models may include convolutional neural networks or transformer neural networks trained to perform specific downstream tasks. In one or more embodiments, downstream tasks may include Disease prediction wherein a Classification model nay be used to classify signals to diseases. Downstream tasks may further include, parameter extraction wherein a regression model may be used to predict the ECG parameters like PR interval, ventricular rate, QT interval and the like. IN one or more embodiments, downstream tasks may further include ECG delineation wherein a segmentation model may be configured to segment ECG signals into P, QRS, T, U waves and the like. In one or more embodiments, downstream tasks may further include ECG rhythm and abnormalities predictions wherein Multiclass classification models are to predict various abnormalities in ECG like rhythm/rhythm abnormalities, conduction abnormalities, morphological abnormalities and the like. In one or more embodiments, downstream tasks may further include ECG text report generation, wherein Auto-regressive models are configured to generate ECG text reports. In one or more embodiments, downstream tasks may further include monitoring applications wherein the focus may shift from a single ECG to tracking changes over time. By comparing paired ECGs from the same patient, the system can identify trends that might signal developing heart problems. In one or more embodiments, downstream tasks may further include advanced parameter prediction machine learning models can estimate various heart-related parameters, including, but not limited to, Ejection Fraction (EF): Measures heart pumping efficiency, Left Ventricular Mass Index (LVMI): Indicates heart muscle thickness, Filling Pressures: Pressure within heart chambers before contraction, Chamber Volumes and Surface Areas: Estimates of heart chamber sizes, Number of Pulmonary Veins (PVs): Detects abnormalities in blood vessels from lungs to the heart, Valve and Vessel Dimensions: Assesses size and function of heart valves and major blood vessels, Vascular Pressures: Estimates pressure within blood vessels and the like. In one or more embodiments, downstream tasks may further include monitoring mechanical and anatomical parameters of the heart through the use of ECG images, such as standardized data. In one or more embodiments, parameters include may include aortic valve diameter, number of pulmonary veins (PVs), and volumetric measurements of chambers (e.g., surface area and volume). In one or more, ECG machine learning model 168 may be configured to perform one or more downstream tasks as described above. In one or more embodiments, ECG machine learning model 168 may be configured to determine similarities and differences between two sets of ECG signals. For example, and without limitation ECG machine learning model 168 may be configured to identify similarities and/or differences between two particular sets of ECG signals such as but not limited to, changes in waveform, changes in amplitude and the like.

With continued reference to FIG. 1, processor 108 is configured to train and/or pre-train an ECG machine learning model 168 as a function of standardized data 164. "Pretraining a machine learning model" as referred to herein refers to a computational process in which a machine learning model is trained on a large data set to learn general features or representation before fine tuning the machine learning model for a specific task. For example, and without limitation, pre-training ECG machine learning model 168 may include determining waveform patterns, heart rate variability, and other relevant characteristics of the ECG signals 124 within the images of standardized data 164. In one or more embodiments, pretraining ECG machine learning model 168 may allow for ECG machine learning model 168 to make determinations on unlabeled training data such as but not limited to determination associated with edge detection, patterns and the like. In one or more embodiments, ECG machine learning model 168 may make determinations on modified ECG data 118 such as relevant features, patterns and the like wherein the determinations may be used as training data when fine tuning ECG machine learning model 168 for a particular cardiac related purpose. In one or more embodiments, pretraining ECG machine learning model 168 may allow for unlabeled training data such as standardized data 164 to be used for multiple purposes. For example, and without limitation, standardized data 164 may be used to determine cardiac abnormalities in one machine learning model and used to determine heart diseases in another machine learning model. In one or more embodiments, pretraining a machine learning model may allow for a machine learning model to leverage general knowledge from a broad dataset, such as standardized data 164, in order to better generate outputs using a limited labeled training data set. In one or more embodiments, pretraining ECG machine learning model 168 may allow for determinations of relevant features, patterns, and the like within standardized data 164 prior to training ECG machine learning model 168 for a particular and/or specific use. In one or more embodiments, ECG machine learning model 168 may contain labeled training data containing inputs such as ECG signals 124 and correlated disease states, disease classifications and the like. In an embodiment, labeled training data may be used to make determinations about standardized data 164 in order to create a larger set of training data. In one or more embodiments, pretraining may allow for iterative training of ECG machine learning model 168 absent human input. In an embodiment, processor 108 may be configured to receive nonconforming data associated with patients, generate standardized data 164, and pretrain ECG machine learning model 168 to determine relevant features, patterns and the like. In an embodiment, ECG machine learning model 168 may be pre-trained following receipt of standardized data 164. In one or more embodiments, ECG machine learning model 168 may be iteratively trained with large data sets containing ECG signals 124 in a standardized format. In one or more embodiments, pretraining ECG machine learning model 168 may include utilizing an unlabeled training data set such as standardized data 164 to generate its own labels based on the unlabeled training data received.

With continued reference to FIG. 1, pretraining ECG machine learning model 168 may include a process in which portions of standardized data 164 are masked and ECG machine learning model 168 and/or processor 108 predicts the missing or masked portions. For example, and without limitation, ECG machine learning model 168 may predict missing portions of a standardized image 136 that has been masked wherein ECG machine learning model 168 may compare predictions to the actual information contained within standardized data 164. In one or more embodiments, ECG machine learning model 168 may be configured to receive modified set of standardized data 164 wherein the modified set may include portions of standardized data 164 that has been masked wherein ECG machine learning model 168 may be tasked with determining masked portions of modified set of standardized data 164. In one or more embodiments, ECG machine learning model 168 may be configured with a pretext task using modified set of standardized data 164. In one or more embodiments, the pretext task may include predicting and/or finding missing portions of images within standardized data 164. In one or more embodiments, ECG machine learning model 168 may extract relevant features from standardized data 164 in order to predict missing portions. In one or more embodiments, ECG machine learning model 168 may contain a predetermined set of values of parameters wherein the parameters refer to weights and biases. In one or more embodiments, parameters may be initialized randomly or received from similar machine learning models. In one or more embodiments, during pretraining, parameters of ECG machine learning model 168 may be given initial values wherein the parameters may change in order to fine tune machine learning model for a specific purpose. In one or more embodiments, pretraining involves modifying parameters before training of the machine learning model based on the input data such as standardized data 164 in order to learn meaningful representations or features that can be further refined further on in order fine tune ECG machine learning model 168 for a specific task. In one or more embodiments, ECG machine learning model 168 may receive as an input modified set of Standardized data 164 and predict standardized data 164. In one or more embodiments, ECG machine learning model 168 may compare predictions of the modified set to standardize data. In one or more embodiments, ECG machine learning model 168 may utilize a loss function in order to measure the discrepancy between predicted outputs of ECG machine learning model 168 and the actual standardized data 164. In one or more embodiments, ECG machine learning model 168 may adjust parameters iteratively through optimization techniques such as, but not limited to gradient descent to minimize the discrepancy.

In one or more embodiments, a machine learning model such as ECG machine learning model 168 may contain parameter values 156 similar to that of ECG transformation model 152. In one or more embodiments, parameter values

156 may be adjusted during training or pretraining in order to minimize a loss function. In one or more embodiments, during training, predicted outputs of the machine learning model are compared to actual outputs wherein the discrepancy between predicted output and actual outputs are measured in order to minimize a loss function. A loss function also known an "error function" may measure the difference between predicted outputs and actual outputs in order to improve the performance of the machine learning model. A loss function may quantify the error margin between a predicted output and an actual output wherein the error margin may be sought to be minimized during the training process. The loss function may allow for minimization of discrepancies between predicted outputs and actual outputs of the machine learning model. In one or more embodiments, the loss function may adjust parameter values 156 of the machine learning model. In one or more embodiments, in a linear regression model, parameter values 156 may include coefficient assigned to each feature and the bias term. In one or more embodiments, in a neural network, parameter values 156 may include weights and biases associated with the connection between neurons or nodes within layers of the network. In one or more embodiments, during training and/or pretraining of the machine learning model, parameter values 156 of the machine learning model may be adjusted as a function of at least one predicted image within standardized data 164 and the actual image within standardized data 164. In one or more embodiments, processor 108 may be configured to minimize a loss function by adjusting parameter values 156 of ECG machine learning model 168 based on discrepancies between predicted outputs and actual outputs. In one or more embodiments, processor 108 may be configured to iteratively pretrain ECG machine learning model 168, wherein processor 108 may be configured to iteratively receive standardized data 164 and adjust parameter values 156 of ECG machine learning model 168. In an embodiments, ECG machine learning model 168 may be pretrained using only standardized images 136 such that learned features are only correlated to the ECG signals 124 and not the changes in image quality or orientation. In one or more embodiments, pretraining the ECG machine learning model 168 as a function of the standardized data 164 includes masking one or more images within the standardized data 164 and predicting outputs of the ECG machine learning model 168 as a function of the one or more masked images. In one or more embodiments, processor 108 may compare masked images to predicted outputs of ECG machine learning model 168 and adjust parameter values 156 until predicted outputs are similar to that of the masked images.

With continued reference to FIG. 1, pretraining ECG machine learning model 168 may include the use of one or more autoencoder models. An autoencoder model is a machine learning model used for unsupervised machine learning in which inputs are transformed into compressed form of the input data and the inputs are re-created using the compressed form of data. In one or more embodiments, autoencoder model learns a compressed representation of data wherein autoencoder model may determine relevant features of the data. In one or more embodiments, autoencoder model minimizes reconstruction error by adjusting parameter values 156 in order to recreate the input. In one or more embodiments, autoencoder model may receive standardized data 164 as an input, compress standardized data 164 and attempt to recreate standardized data 164 from the compressed standardized data 164. In one or more embodiments, autoencoder model may learn representations between images by compressing images into a lower latent space. In one or more embodiments, compression may include the process of removing noise or unwanted signals to remove excess information from standardized images 136 within standardized data 164. In one or more embodiments, autoencoder model may be configured to capture important representation of standardized data 164 during compression wherein ECG models may be reconstructed during decoding. In one or more embodiments, autoencoder model may compare encoded inputs to decoded inputs in order to adjust parameter values 156 of the autoencoder model. In one or more embodiments, retraining ECG machine learning model 168 may include training autoencoder model to reduce reconstruction error when reconstructing compressed inputs such as ECG data 118. In one or more embodiments, autoencoder model may capture meaningful representations during compression such as irregular patterns, frequencies and the like. In one or more embodiments, autoencoder model may be used to detect anomalies within standardized data 164 wherein autoencoder model may be trained with standardized data 164 representing regular heart activity such that reconstruction of anomalies may indicate a higher reconstruction error and thereby an issue. In one or more embodiments, autoencoder model may contain an encoding function in which input data is transformed and/or compressed. In one or more embodiments, autoencoder model may contain a decoding function in which input data is recreated from the transformed or compressed data. In one or more embodiments, autoencoder model may be iteratively trained to reduce construction loss wherein construction loss refers to the accuracy of the decoded output in comparison to the input. In one or more embodiments, autoencoder model may capture only those variations in data that are needed to reconstruct the input. For example, and without limitation, autoencoder model may capture only those patterns, frequencies, outliers and the like within a set of standardized data 164 in order to recreate the set of ECG signals 124 within standardized data 164. In one or more embodiments, autoencoder model may be used to compare sets of ECG signals 124 within standardized data 164 wherein ECG signals 124 containing similar patterns, frequencies and the like may indicate some sort of likeness.

With continued reference to FIG. 1, processor 108 may utilize a masked autoencoder technique to train ECG machine learning model 168. A masked autoencoder technique refers to a process in which the input data is modified such that various portions are masked or removed and the autoencoder model is configured to reconstruct the original input data. In one or more embodiments, a masked autoencoder model may be configured to receive an input such as a modified set of Standardized data 164 and be configured to reconstruct standardized data 164. In one or more embodiments, masked autoencoder model can be used for denoising and/or anomality detection. In one or more embodiments, masked autoencoder model may be configured to remove noise from ECG signals 124 wherein reconstructed outputs may include the missing portions of the ECG signals 124 as well as the noise removed. In one or more embodiments, masked autoencoder model can further be trained on normal ECG signals 124 and/or abnormal ECG signals 124 within standardized in order to whether an ECG signal 124 may be determined to be normal or abnormal. In one or more embodiments, masked autoencoder model may be configured with finding similarities between multiple ECG signals 124 in order to determine similarities between normal and abnormal ECG signals 124. In one or more embodiments, masked autoencoder model may contain one or more parameter values 156 that are sought to be adjusted during training. In one or more embodiments, the parameter values 156 may be used for other machine learning models in order to find similarities between ECG signals 124. In one or more embodiments, parameter values 156 of masked autoencoder model, such as but not limited to model architecture parameters, training parameters, regularization parameters and the like may be iteratively adjusted in order to minimize discrepancies between predicted standardized images 136. In one or more embodiments, masked autoencoder model may be configured to reconstruct standardized data 164 based on inputs such as modified set of standardized data 164 wherein parameter values 156 may be adjusted based on discrepancies between the reconstructed output and masked images. In one or more embodiments, masked autoencoder model may be trained using backpropagation and gradient descent to minimize the reconstruction error between the output of the decoder and the original mased image.

With continued reference to FIG. 1, processor 108 may be configured to train ECG machine learning model 168 as a function of one or more parameter values 156 of ECG machine learning model 168 and a labeled set of training data. A "labeled set of training data" or "labeled training data" as referred to herein refers to training data that has been labeled such that the training data contains inputs and correlated labeled outputs. For example, and without limitation, labeled training data may include inputs such as ECG signals 124 and correlated outputs labeling the ECG signals 124 with various cardiac abnormalities, abnormal heart rhythms and the like. In one or more embodiments, labeled training may include inputs such as ECG signals 124 and/or images of ECG signals 124 and correlated outputs indicating abnormalities, wave patterns, arrhythmia and/or other heart conditions. In one or more embodiments, labeled training data may be generated by a user, $3^{rd}$ party and the like. In one or more embodiments, labeled training data may be received from previous iterations of the processing wherein previously received ECG signals 124 may be given a label through user input in order to increase the amount of labeled training data. In one or more embodiments, labeled training data may be iteratively refined and/or modified in order to ensure that inputs contain correct labels and/or correlated outputs. In one or more embodiments, A set of labeled training data may include labeled training data for a particular purpose associated with heart abnormalities. For example, and without limitation, set of labeled training data may include training data exclusively for classification, training data exclusively for pattern recognition, Training data for predicting previous abnormalities, training data for predicting future abnormalities and the like.

With continued reference to FIG. 1, processor 108 may finetune a pre-trained machine learning model, such as ECG machine leaning model, that has been trained on a large set of unlabeled training data. In one or more embodiments, ECG machine learning model 168 may be pre trained to identify patterns and features within ECG signals 124. In one or more embodiments, processor 108 may feed ECG machine learning model 168 with labeled training data in order to adjust the parameters of ECG machine learning model 168 to generate outputs associated with ECG signals 124. In one or more embodiments, processor 108 may update parameters using one or more back propagation techniques. In one or more embodiments, backpropagation techniques may include a processor 108 feeding error rates through a neural network to make the neural network more accurate. In one or more embodiments, errors between the machine learning models predictions and true labels are used to update the model's weights such as parameter values 156. In one or more embodiments, labeled training data may be used to predict outputs associated with an ECG signal 124 or a standardized image 136 of an ECG signal 124 wherein outputs of ECG machine learning model 168 may be compared to the true value of the outputs as indicated by labeled training data. In one or more embodiments, regularization techniques such as dropout of weight decay may be used in order to prevent ECG machine learning model 168 from memorizing the small set of labeled training data. In one or more embodiments, training ECG machine learning model 168 may include fine tuning already generated parameter values 156 for a particular purpose.

In one or more embodiments, processor 108 may use one or more transfer learning processes to train ECG machine learning model 168. In one or more embodiments, fine tuning may include a process in which insights, features, representations and the like generated during a pre-training phase can be used and applied to current machine learning models. For example, and without limitation, representations learned using standardized data 164 may be applied to various machine learning models to generate more accurate outputs. In one or more embodiments, processor 108 may use one or more feature extraction processes to extract high level representations of the data received and use those high level representations as inputs into the new model. In one or more embodiments, transfer learning may allow for learned features to be fine-tuned to a specific task or process. For example, and without limitation, extracted features may include recognizing particular patterns, frequencies and the like wherein said particular patterns and frequencies may be used to identify abnormalities. In one or more embodiments, during transfer learning the new model is initialized from weights, parameter values 156 and the like generated during pre-training. In one or more embodiments, parameter values 156 may then be fine-tuned by introducing a labeled training data set. In one or more embodiments, learned representations may be used to identify abnormalities in ECG signals 124, classify patterns in ECG signals 124 to disease states and the like. In one or more embodiments, pretraining ECG machine learning model 168 may allow for generalization wherein ECG machine learning model 168 may be configured to adapt to new unseen data due to the vast amount of standardized data 164 received. In one or more embodiments, a smaller dataset of labeled training data may prevent generalization as the machine learning model may not be trained to properly analyze unseen data. In one or more embodiments, pre training ECG machine learning model 168 may allow for generalization. In one or more embodiments, ECG machine learning model 168 may be trained following each iteration of system 100. In one or more embodiments, a user may iteratively provide feedback in order to train ECG machine learning model 168. In one or more embodiments, ECG machine learning model 168 may be pretrained using a large data set in order to reduce the training of ECG machine learning model 168. In one or more embodiments, pre training ECG machine learning model 168 may allow for more accurate outputs and as a result, less computational power needed to iteratively train ECG machine learning model 168.

With continued reference to FIG. 1, ECG machine learning model 168 may be configured to receive one or more standardized images 136 and/or ECG inputs 172 associated with a patient and output one or more diagnostic labels 178 associated with the patient. in an embodiment, ECG inputs 172 may include ECG signals 124 contained within an image of standardized format. As used in the current disclosure, a "diagnostic label" is a label used describe a specific condition, disorder, or illness that affects an individual's health or heart structure or function. A diagnostic label 178 may be any specific condition, disorder, or illness, specifically associated with the heart. In a non-limiting example, diagnostic labels 178 may be associated with conditions related to the cardiac health such as normal sinus rhythm, atrial fibrillation, myocardial infarction, ventricular tachycardia, bundle branch bloc, arrythmias, ischemic heart disease, heart enlargement, conduction abnormalities, cardiac ischemia, electrolyte imbalances, and the like. Processor 108 may assign a diagnostic label 178 to a patient as function of an ECG input 172 received. In one or more embodiments. ECG training data may contain a plurality of ECG inputs 172 and correlated diagnostic labels 178. In an embodiment, ECG training data may be generated by a user, 3rd party or the like. In one or more embodiments, ECG training data may be received from electronic health records containing ECG inputs 172 and correlated diagnostic labels 178.

With continued reference to FIG. 1, ECG inputs 172 may include images of ECG signals 124. In one or more embodiments, processor 108 may be configured to perform image classification using an image classifier wherein processor 108 may be configured to detect various features of ECG inputs 172 and assign diagnostic labels 178 based on the various features. An "image classifier," as used in this disclosure is a machine-learning model, such as a mathematical model, neural net, or program generated by a machine-learning algorithm known as a "classification algorithm," as described in further detail below, that sorts inputs of image information into categories or bins of data, outputting the categories or bins of data and/or labels associated therewith. Image classifier may be configured to output at least a datum that labels or otherwise identifies a set of images that are clustered together, found to be close under a distance metric as described below, or the like. Computing device 104 and/or another device may generate image classifier using a classification algorithm, defined as a process whereby computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In some cases, processor 108 may use an image classifier to identify a key image in data described in any data described in this disclosure. As used herein, a "key image" is an element of visual data used to identify and/or match elements to each other. An image classifier may be trained with binarized visual data that has already been classified to determine key images in any other data described in this disclosure. "Binarized visual data" for the purposes of this disclosure is visual data that is described in binary format. For example, binarized visual data of a photo may be comprised of ones and zeroes wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g. ECG inputs 172 and/or images of ECG signals 124, such as images similar to standardized data 164) described in this disclosure and output a key image with the data. In an embodiment, image classifier may be used to compare visual data in data such as ECG inputs 172 with visual data in another data set. Visual data in another data set may include a plurality of visual data retrieved from database 116. In some cases, image classifier may identify one or more components within ECG input 172. In some cases, image classifier may classify various vector loops, various cardiac vectors, and the like within ECG input 172. In one or more embodiments, a particular vector loop, cardiac vector and the like within the image may be associated with a particular diagnostic label 178.

With continued reference to FIG. 1, processor 108 may employ pattern matching techniques to identify specific patterns or abnormalities within the ECG input 172 to generate diagnostic label 178. This can involve comparing specific segments, intervals, or waveforms of the ECG input 172 to detect similarities or differences. Cross-correlation, template matching, or dynamic time warping algorithms may be used for this purpose. Processor 108 may perform statistical analysis on various parameters derived from the ECG input 172 to generate diagnostic label 178. This can involve calculating means, standard deviations, or other statistical measures for specific features or segments of the ECG input 172. By comparing these statistical parameters, the computer can identify significant differences or similarities between the ECG input 172 and a reference image. In one or more embodiments, ECG machine learning model 168 may include a machine learning model configured to receive images as inputs and output diagnostic label 178. In one or more embodiments, ECG machine learning model 168 may be trained using standardized data 164.

With continued reference to FIG. 1, processor 108 may be configured to create a user interface data structure. As used in this disclosure, "user interface data structure" is a data structure representing a specialized formatting of data on a computer configured such that the information can be effectively presented for a user interface. User interface data structure may include ECG machine learning model 168 and/or any other data as described in this disclosure. In one or more embodiments, user interface data structure may allow for interaction with ECG machine learning model 168 to receive generated outputs.

With continued reference to FIG. 1, processor 108 may be configured to transmit the user interface data structure to a graphical user interface. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. Processor 108 may transmit the data described above to database 116 wherein the data may be accessed from database 116. Processor 108 may further transmit the data above to a device display or another computing device 104.

With continued reference to FIG. 1, system 100 may include a graphical user interface (GUI). For the purposes of this disclosure, a "user interface" is a means by which a user and a computer system interact. For example, through the use of input devices and software. In some cases, processor 108 may be configured to modify graphical user interface as a function of the inputs and outputs of ECG machine learning model 168 by populating user interface data structure and visually presenting the data through modification of the graphical user interface. A user interface may include graphical user interface, command line interface (CLI), menu-driven user interface, touch user interface, voice user interface (VUI), form-based user interface, any combination thereof and the like. In some embodiments, a user may interact with the user interface using a computing device 104 distinct from and communicatively connected to processor 108. For example, a smart phone, smart tablet, or laptop operated by the user and/or participant. A user interface may include one or more graphical locator and/or cursor facilities allowing a user to interact with graphical models and/or combinations thereof, for instance using a touchscreen, touchpad, mouse, keyboard, and/or other manual data entry device. A "graphical user interface," as used herein, is a user interface that allows users to interact with electronic devices through visual representations. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in graphical user interface. Persons skilled in the art, upon reviewing the entirety of this disclosure, will be aware of various ways in which a graphical user interface and/or elements thereof may be implemented and/or used as described in this disclosure. In one or more embodiments, graphical user interface may include a graphical visualization of the human heart and various locations as to which attention may be needed. In one or more embodiments, diagnostic label 178 may be used to pinpoint the components of the heart that are acting abnormally and indicate the exact issue.

With continued reference to FIG. 1, system 100 may further include a display device communicatively connected to at least a processor 108. "Display device" for the purposes of this disclosure is a device configured to show visual information. In some cases, display device may include a liquid crystal display (LCD), a cathode ray tube (CRT), a plasma display, a light emitting diode (LED) display, and any combinations thereof. Display device may include, but is not limited to, a smartphone, tablet, laptop, monitor, tablet, and the like. Display device may include a separate device that includes a transparent screen configured to display computer generated images and/or information. In some cases, display device may be configured to visually present one or more data through GUI to a user, wherein a user may interact with the data through GUI. In some cases, a user may view GUI through display.

With continued reference to FIG. 1, system 100 may include and/or be included within a mobile unit. "Mobile unit" for the purposes of this disclosure is a device that is capable of being transported from one location to another. In one or more embodiments, mobile unit may include wheels that allow mobile unit to be moved from one location to another. In one or more embodiments, display device may be located atop mobile unit wherein a user may navigate mobile unit with display device around a room. In one or more embodiments, mobile unit may contain a battery pack wherein computing device 104 may be powered by battery back. In one or more embodiments, battery pack may be rechargeable. In one or more embodiments, one or more processes as described above, such as but not limited to processing relating to machine learning models, may be computed on a cloud, network server and the like to save on battery power. In one or more embodiments, mobile unit may allow for system to be navigated throughout an operating room. In one or more embodiments, location of mobile unit may differ for each patient and/or procedure. In one or more embodiments, sensors as described above may be connected to mobile unit wherein mobile unit may be navigated closer to and/or further away from patient based on the location of sensors. In one or more embodiments, sensors may contain wiring that needs to be physically connected to mobile unit. In one or more embodiments, mobile unit may allow for movement of system from one location to another in instances in which movement may be needed. In one or more embodiments, mobile unit may allow for receipt of ECG inputs 172 from a patient in order to generate diagnostic labels 178.

Figure 2:
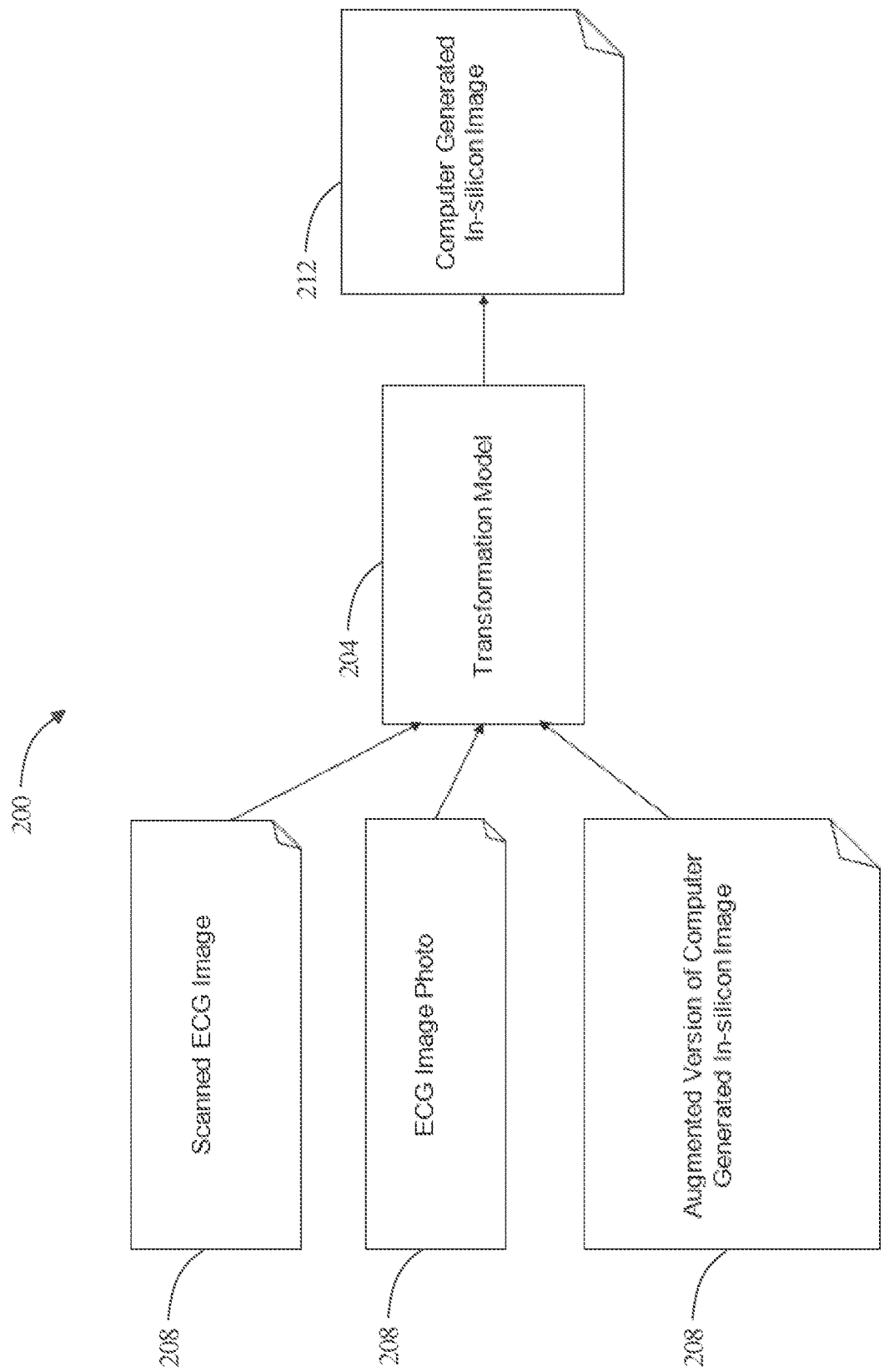
FIG. 2 is an exemplary embodiment of a system for transforming images in accordance with the subject disclosure.

Referring now to FIG. 2, an exemplary embodiment of a system 200 for transforming images is described. In one or more embodiments, system include a transformation model 204 is described. In one or more embodiments, transformation model 204 may include ECG transformation model as described above. In one or more embodiments, inputs 208 into transformation model 204 may include inputs 208 such as scanned ECG images, ECG images photos taken by a camera and and/or augmented versions of computer generated images. Transformation model 204 may receive inputs and generate outputs 212. In one or more embodiments, outputs may include standardized images as described above. In one or more embodiments, outputs may include computer generated-in silicon images. Transformation model 204 may be trained by taking in either augmented version of computer generated in-silicon images or photo/scanned copy of printed ECG or screenshot of ECG as input and would be optimized to produce a pristine computer generated in-silicon quality image as described in reference to FIG. 1. The transformation model 204 would output the same layout as the input layout. transformation model 204 may include a convolutional neural networks or transformer based neural networks or a combination of both. In one or more embodiments, transformation model 204 may include a Pix2Pix model, wherein the Pix2Pix model is a generative adversarial network that allows for image to image translation. In one or more embodiments, Pix2Pix model may be trained by taking in either augmented version of computer generated in-silicon images or photo/scanned copy of printed ECG signals such as ECG image as described above or screenshot of ECG as input and would be optimized to produce a pristine computer generated in-silicon quality image such as EG visual data as described above. In one or more embodiments, Pix2Pix model may be trained to map input images from one domain such as ECG images to output images in another domain, such as ECG visual data. In one or more embodiments, Pix2Pix model may be trained using a data set of ECG images correlated to ECG visual data as described above. IN one or more embodiments, Pix2Pix model may be trained to receive images of ECG signals associated with patients and generate in-silicon images which may be used by one or more machine learning models as described in this disclosure.

Figure 3:
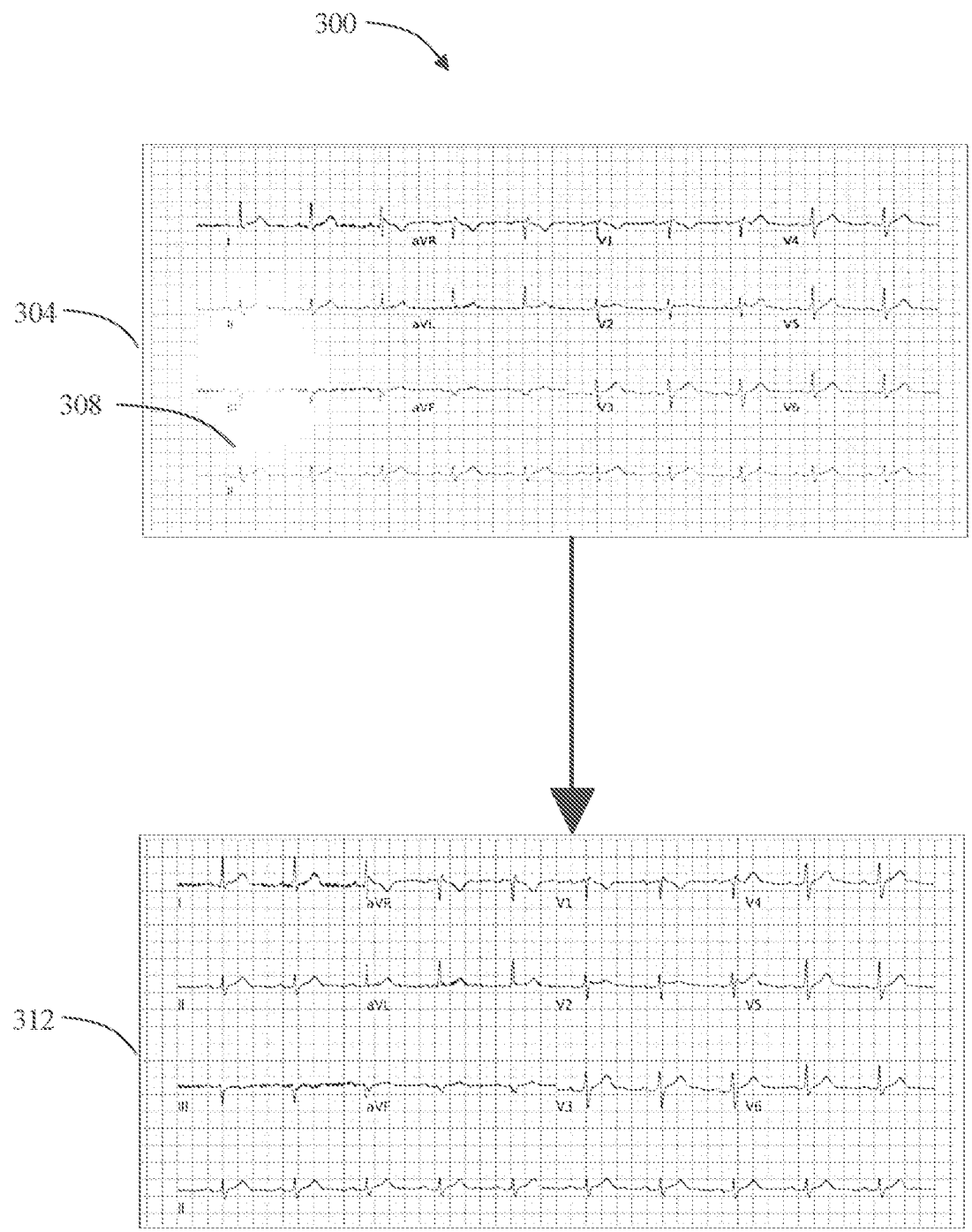
FIG. 3 is an exemplary process of transforming images of ECG signals in accordance with the subject disclosure.

Referring now to FIG. 3, an exemplary process 300 of transforming images of ECG signals is described. In one or more embodiments, process 300 may include receiving an input image 304. In one or more embodiment, input image 304 may include an image taken by a camera, a scanner and the like. As Illustrated in FIG. 3, input image 304 may contain deformities 308 that may cause issues with processing input image 304. In one or more embodiments, input image 304 may include ECG image data and/or non-conforming data as described in reference to FIG. 1. In one or more embodiments, input image 304 may include a 3×4 with 1 Rhythm lead layout wherein the input image 304 depict 3 leads placed across 4 rows with one additional lead dedicated to displaying rhythm. In one or more embodiments, process 300 may include the use of a transformation model such as ECG transformation model to convert input image 304 into output image 312. In one or more embodiments, output image 312 may include a computer generated image of ECG signals. In one or more embodiments, output image may include a 3×4 with 1 Rhythm lead layout similar to that of input image 304. In one or more embodiments, corrections to an image with an ECG signal may be made without modifying the original ECG signal being depicted. In one or more embodiments, output image 312 may include a computer generated in-silicon image. In one or more embodiments, output image may now be used within ECG machine learning model as described above in order to generate a diagnostic output. In one or more embodiments, output image may include standardized image as described above. In one or more embodiments, output image 312 may include an image that may be contained within standardized data as described above. In one or more embodiments, process 300 may depict a transformation process in which a non-conforming image has been converted into a standardized image.

Figure 4:
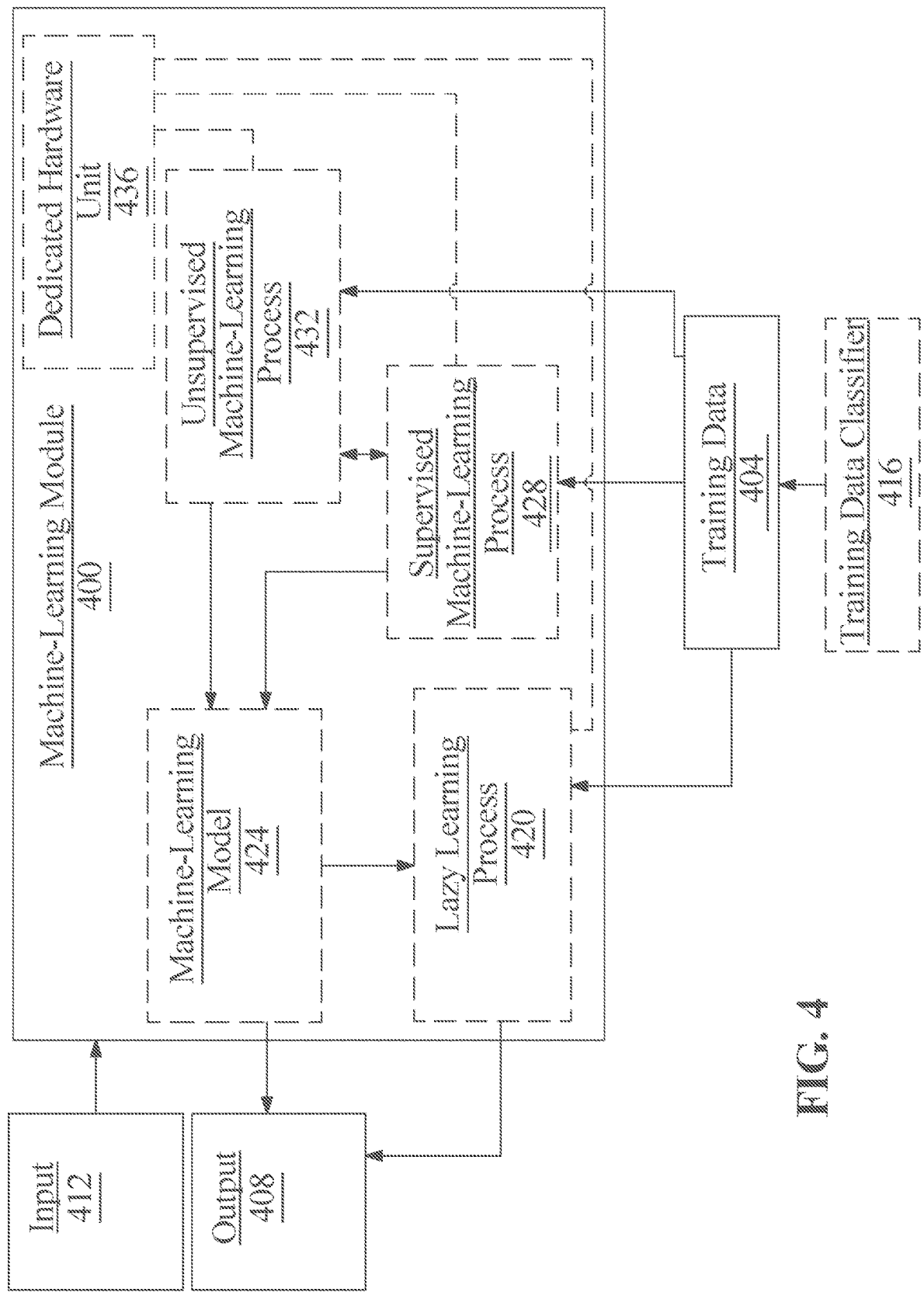
FIG. 4 is a block diagram of an exemplary machine-learning process.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example inputs may include inputs such as non-conforming data and outputs may include outputs such as standardized data.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to layouts of ECG images wherein ECG images may be classified to layouts such as 3×4, 6×2 and the like as described in reference to FIG. 1.

Still referring to FIG. 4, a computing device, such as any computing device as described in this disclosure may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)±P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\Sigma_{i=0}^{n} a_i^2},$$

where $\alpha_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the 25$^{th}$ percentile value and the 50$^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs such as non-conforming data and/or ECG image data as described above as inputs, outputs such as ECG visual data and/or standardized data as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
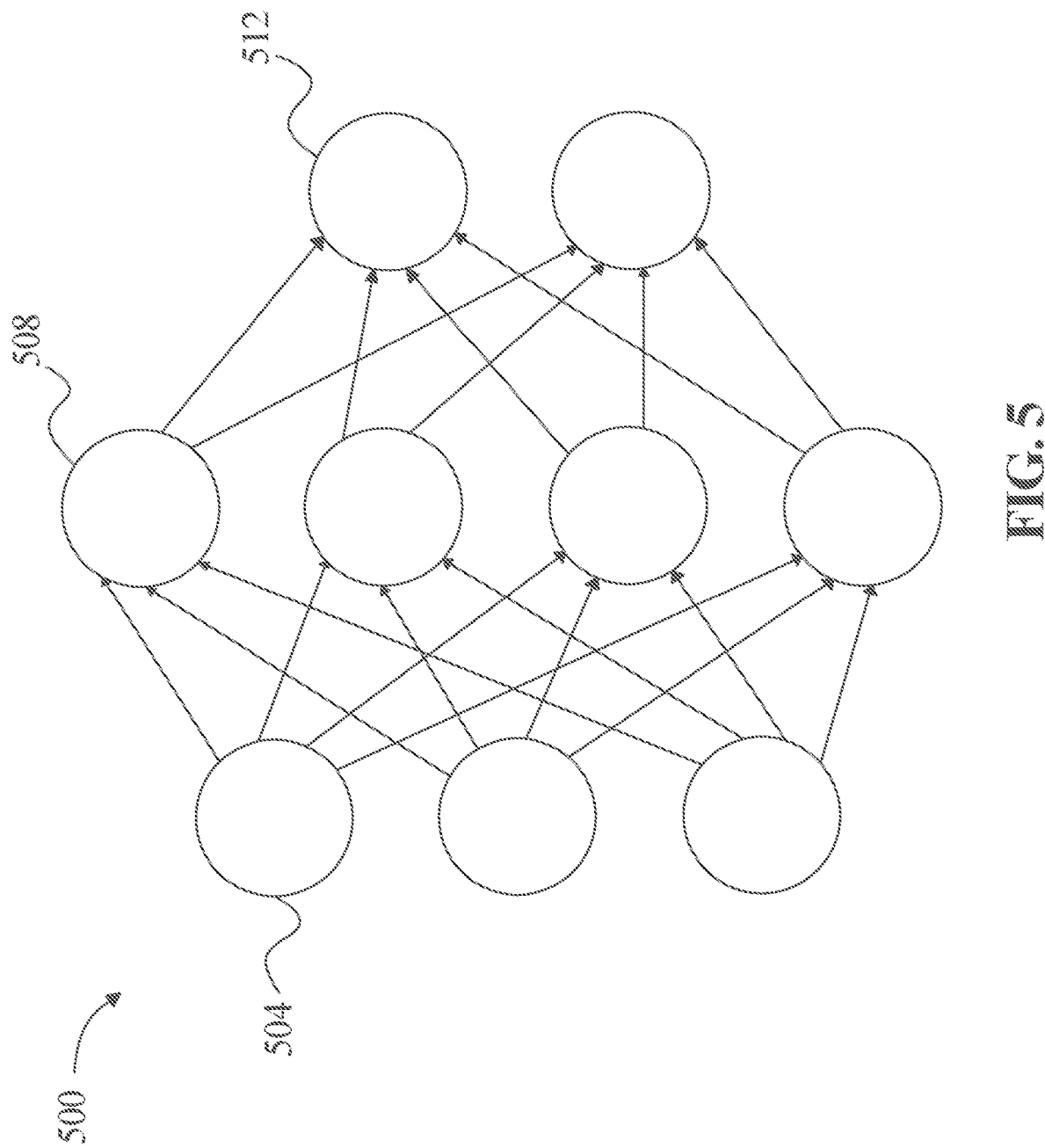
FIG. 5 is a diagram of an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
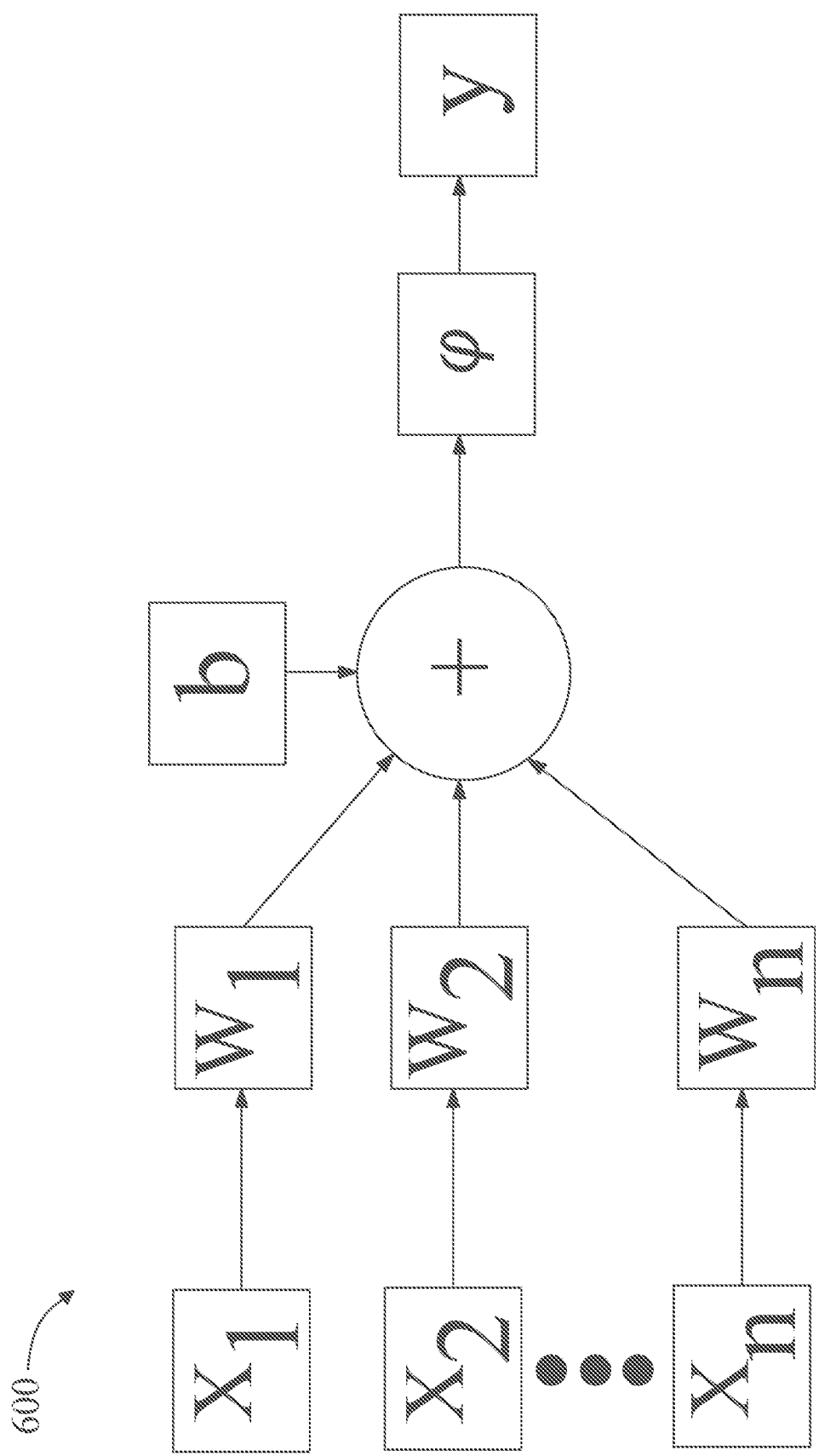
FIG. 6 is a diagram of an exemplary embodiment of a node of a neural network.

Referring now to FIG. 6, an exemplary embodiment of a node 600 of a neural network is illustrated. A node may include, without limitation a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some $\alpha$, an exponential linear units function such as $$f(x) = \begin{cases} x & \text{for } x \geq 0 \\ \alpha(e^x - 1) & \text{for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $$f(x) = a\left(1 + \tanh\left(\sqrt{2/\pi}\,(x + bx^r)\right)\right)$$

for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
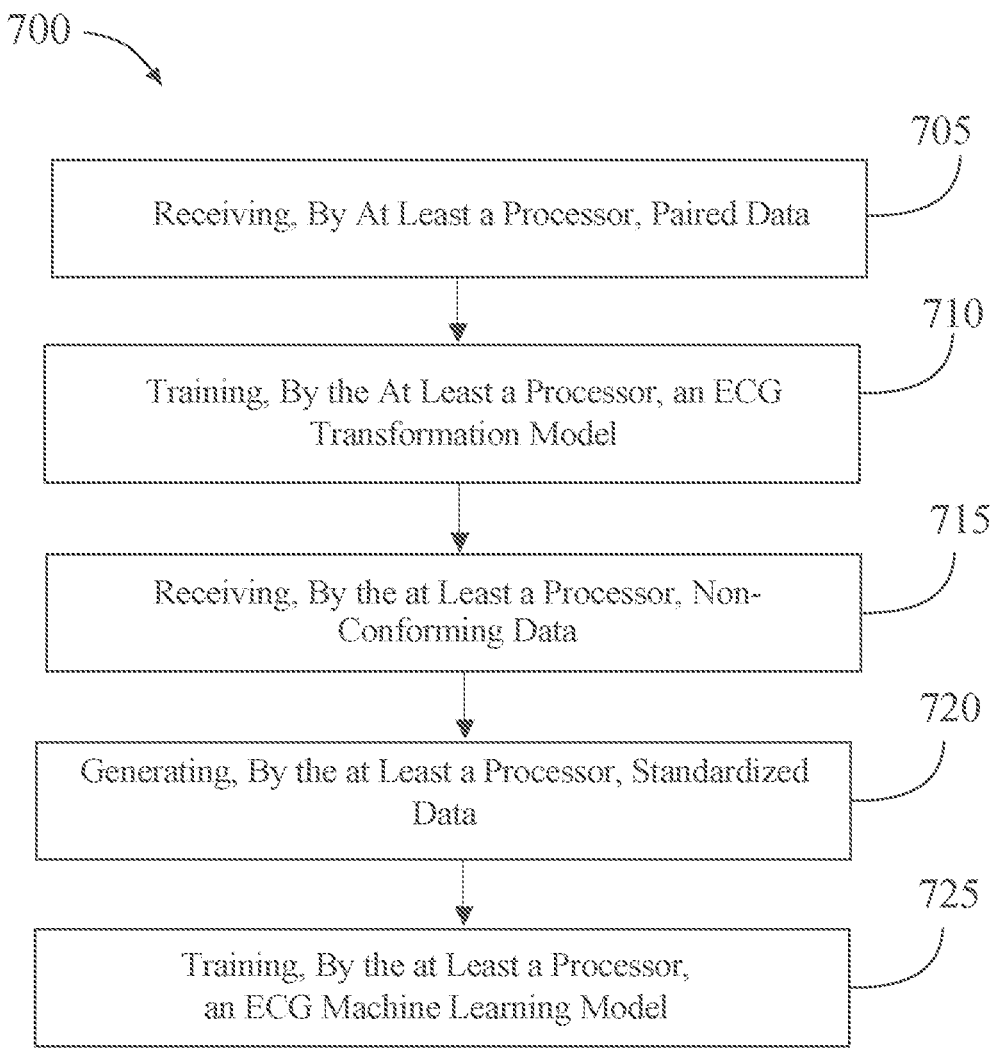
FIG. 7 is a flow diagram illustrating an exemplary embodiment of a method for transforming electrocardiogram images for use in one or more machine learning models.

Referring now to FIG. 7, an exemplary method 700 for transforming electrocardiogram images for use in one or more machine learning models is described. At step 705, method 700 includes receiving, by at least a processor, paired data including a plurality of ECG images correlated to a plurality of standardized images, wherein each ECG image of the plurality of ECG images is correlated with each standardized image of the plurality of standardized images. In one or more embodiments, receiving, by the at least a processor, the paired data includes receiving ECG data including a plurality of electrocardiogram (ECG) signals in a textual format, generating ECG visual data as a function of the ECG data, wherein the ECG visual data includes the plurality of standardized images and receiving ECG image data including the plurality of ECG images associated with the ECG data, generating the paired data as a function of the ECG image data and the plurality of ECG images. In one or more embodiments, receiving, by the at least a processor, the paired data including the plurality of ECG images correlated to the plurality of standardized images further includes augmenting at least one ECG image of the plurality of ECG images. In one or more embodiments, the plurality of standardized images include a plurality of in-silicon images. In one or more embodiments, the plurality of ECG images includes a plurality of non-conforming images. In one or more embodiments, the standardized data includes unlabeled training data. In one or more embodiments, generating the ECG visual data includes plotting the ECG data. This may be implemented with reference to FIGS. 1-6 and without limitation.

With continued reference to FIG. 7, at step 710 method 700 includes training, by the at least a processor, an ECG transformation model as a function of the paired data, wherein training the transformation model includes adjusting one or more parameter values of the ECG transformation model as a function of a comparison between at least one predicted standardized image and at least one standardized image of the plurality of standardized images. This may be implemented with reference to FIGS. 1-6 and without limitation.

With continued reference to FIG. 7, at step 715 method 700 includes receiving, by the at least a processor, non-conforming data. This may be implemented with reference to FIGS. 1-6 and without limitation.

With continued reference to FIG. 7, at step 720 method 700 includes generating, by the at least a processor, standardized data as a function of the ECG transformation model and the non-conforming data. This may be implemented with reference to FIGS. 1-6 and without limitation.

With continued reference to FIG. 7, at step 725 method 700 includes training, by the at least a processor, an ECG machine learning model as a function of the standardized data. IN one or more embodiments, the ECG machine learning model is configured to receive one or more inputs associated with a patient and output one or more diagnostic labels associated with the patient. In one or more embodiments, training, by the at least a processor, the ECG machine learning model as a function of the standardized data includes pretraining the ECG machine learning model as a function of the standardized data and training the ECG machine learning model as a function of the standardized data and a labeled training data set. In one or more embodiments, pretraining the ECG machine learning model as a function of the standardized data includes masking one or more images within the standardized data and predicting outputs of the ECG machine learning model as a function of the one or more masked images. This may be implemented with reference to FIGS. 1-6 and without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
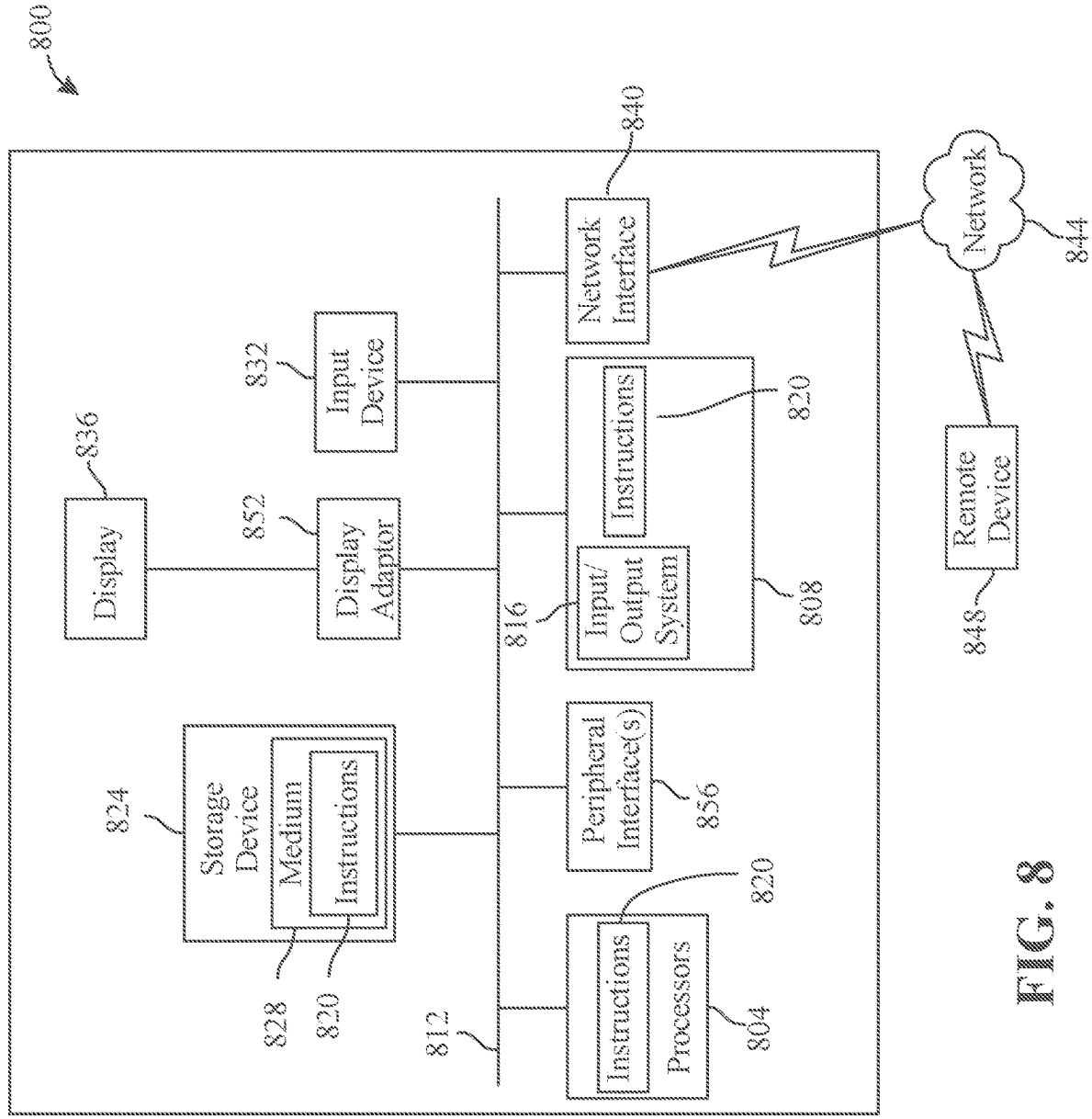
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for transforming electrocardiogram images for use in one or more machine learning models, the system comprising:
   at least a processor; and
   a memory communicatively connected to the at least a processor, the memory containing instructions configuring the at least a processor to:
   receive training data comprising paired data, wherein the paired data comprises a plurality of ECG images as inputs correlated to a plurality of standardized images as outputs, wherein each ECG image of the plurality of ECG images is correlated with each standardized image of the plurality of standardized images;
   sanitize the training data using a dedicated hardware unit comprising circuitry configured to perform signal processing operations, wherein sanitizing the training data comprises:
      determining by the dedicated hardware unit that at least one training data entry of the training data has a signal to noise ratio below a threshold value; and
      removing the at least one training data entry from the training data to create sanitized training data;
   train, iteratively, an ECG transformation model using the sanitized training data comprising the plurality of ECG images correlated to the plurality of standardized images, wherein training the ECG transformation model includes retraining the ECG transformation model with feedback from previous iterations of the ECG transformation model, wherein training the ECG transformation model further comprises:
      adjusting, iteratively, utilizing an optimization technique, one or more parameter values of the ECG transformation model as a function of a comparison between at least one predicted standardized image and at least one standardized image of the plurality of standardized images;
   receive non-conforming data;
   generate standardized data as a function of the trained ECG transformation model and the non-conforming data; and
   train an ECG machine learning model as a function of the standardized data.

2. The system of claim 1, wherein receiving the paired data comprises:
   receiving ECG data comprising a plurality of electrocardiogram (ECG) signals in a textual format;
   generating ECG visual data as a function of the ECG data, wherein the ECG visual data comprises the plurality of standardized images;
   receiving ECG image data comprising the plurality of ECG images associated with the ECG data; and
   generating the paired data as a function of the ECG image data and the plurality of ECG images.

3. The system of claim 2, wherein receiving the paired data further comprises augmenting at least one ECG image of the plurality of ECG images.

4. The system of claim 1, wherein the plurality of standardized images comprises a plurality of in-silicon images.

5. The system of claim 1, wherein the plurality of ECG images comprises a plurality of non-conforming images.

6. The system of claim 1, wherein the standardized data comprises unlabeled training data.

7. The system of claim 2, wherein generating the ECG visual data comprises plotting the ECG data.

8. The system of claim 1, wherein the ECG machine learning model is configured to receive one or more inputs associated with a patient and output one or more diagnostic labels associated with the patient.

9. The system of claim 1, wherein training the ECG machine learning model as a function of the standardized data comprises:
   pretraining the ECG machine learning model as a function of the standardized data; and
   fine-tuning the ECG machine learning model as a function of a labeled training data set.

10. The system of claim 9, wherein pretraining the ECG machine learning model as a function of the standardized data comprises masking one or more images within the standardized data.

11. A method for transforming electrocardiogram images for use in one or more machine learning models, the method comprising:
   receiving, by at least a processor, training data comprising paired data, wherein the paired data comprises a plurality of ECG images as inputs correlated to a plurality of standardized images as outputs, wherein each ECG image of the plurality of ECG images is correlated with each standardized image of the plurality of standardized images;
   sanitizing, by the at least a processor, the training data using a dedicated hardware unit comprising circuitry configured to perform signal processing operations, wherein sanitizing the training data comprises:

determining by the dedicated hardware unit that at least one training data entry of the training data has a signal to noise ratio below a threshold value; and removing the at least one training data entry from the training data to create sanitized training data;

training, iteratively, by the at least a processor, an ECG transformation model using the sanitized training data comprising the plurality of ECG images correlated to the plurality of standardized images, wherein training the ECG transformation model includes retraining the ECG transformation model with feedback from previous iterations of the ECG transformation model, wherein training the ECG transformation model further comprises:

adjusting, iteratively, utilizing an optimization technique, one or more parameter values of the ECG transformation model as a function of a comparison between at least one predicted standardized image and at least one standardized image of the plurality of standardized images;

receiving, by the at least a processor, non-conforming data;

generating, by the at least a processor, standardized data as a function of the trained ECG transformation model and the non-conforming data; and training, by the at least a processor, an ECG machine learning model as a function of the standardized data.

12. The method of claim 11, wherein receiving, by the at least a processor, the paired data comprises:

receiving ECG data comprising a plurality of electrocardiogram (ECG) signals in a textual format;

generating ECG visual data as a function of the ECG data, wherein the ECG visual data comprises the plurality of standardized images;

receiving ECG image data comprising the plurality of ECG images associated with the ECG data; and generating the paired data as a function of the ECG image data and the plurality of ECG images.

13. The method of claim 12, wherein receiving, by the at least a processor, the paired data further comprises augmenting at least one ECG image of the plurality of ECG images.

14. The method of claim 11, wherein the plurality of standardized images comprises a plurality of in-silicon images.

15. The method of claim 11, wherein the plurality of ECG images comprises a plurality of non-conforming images.

16. The method of claim 11, wherein the standardized data comprises unlabeled training data.

17. The method of claim 12, wherein generating the ECG visual data comprises plotting the ECG data.

18. The method of claim 11, wherein the ECG machine learning model is configured to receive one or more inputs associated with a patient and output one or more diagnostic labels associated with the patient.

19. The method of claim 11, wherein training, by the at least a processor, the ECG machine learning model as a function of the standardized data comprises:

pretraining the ECG machine learning model as a function of the standardized data; and fine-tuning the ECG machine learning model as a function of a labeled training data set.

20. The method of claim 19, wherein pretraining the ECG machine learning model as a function of the standardized data comprises masking one or more images within the standardized data.

\* \* \* \* \*